US012773674B2

(12) United States Patent
Ward et al.

(10) Patent No.: US 12,773,674 B2
(45) Date of Patent: *Oct. 27, 2026

(54) USE OF RENEWABLE ENERGY IN OLEFIN SYNTHESIS

(71) Applicant: SABIC Global Technologies B.V., Bergen op Zoom (NL)

(72) Inventors: Andrew Mark Ward, Redcar (GB); Scott Stevenson, Sugar Land, TX (US); Arno Oprins, Geleen (NL); Zhun Zhao, Sugar Land, TX (US); Tim Abbott, Redcar (GB); Kenneth Francis Lawson, Redcar (GB); Joseph William Schroer, Sugar Land, TX (US); Michael Edward Huckman, Sugar Land, TX (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 186 days.

This patent is subject to a terminal disclaimer.

(21) Appl. No.: 18/898,321

(22) Filed: Sep. 26, 2024

(65) Prior Publication Data

US 2025/0010264 A1 Jan. 9, 2025

Related U.S. Application Data

(63) Continuation of application No. 17/310,072, filed as application No. PCT/US2020/013521 on Jan. 14, 2020, now Pat. No. 12,128,378.

(Continued)

(51) Int. Cl.

*B01J 19/00* (2006.01)
*B01D 53/047* (2006.01)

(Continued)

(52) U.S. Cl.

CPC ........ *B01J 19/0053* (2013.01); *B01D 53/047* (2013.01); *B01D 53/265* (2013.01);

(Continued)

(58) Field of Classification Search

CPC ......................... B01J 19/0013; B01J 19/0033; B01J 19/0053; B01J 19/08; B01J 19/2465;

(Continued)

(56) References Cited

U.S. PATENT DOCUMENTS 1,247,520 A 11/1917 Fessenden
2,002,525 A 5/1935 Cambron et al.

(Continued)

FOREIGN PATENT DOCUMENTS

CN 85101024 1/1987
CN 102008972 4/2011

(Continued)

OTHER PUBLICATIONS

Anonymous: "Renewable Electrolysis Hydrogen and Fuel Cells" Oct. 2014 https://www.nrel.gov/hydrogen/renewable-electrolysis.html.

(Continued)

*Primary Examiner* — Bobby Ramdhanie
*Assistant Examiner* — Jason Y Chong
(74) *Attorney, Agent, or Firm* — NORTON ROSE FULBRIGHT US LLP

(57) ABSTRACT

An olefin synthesis plant comprising: a feed pretreatment section configured to pretreat a feed stream; a pyrolysis section comprising one or more pyrolysis reactors configured to crack hydrocarbons in the feed stream in the presence of a diluent to produce a cracked gas stream; a primary fractionation and compression section configured to provide heat recovery from and quenching of the cracked gas stream; remove a component from the cracked gas stream; and (Continued)

compress the cracked gas stream, thus providing a compressed cracked gas stream; and/or a product separation section configured to separate a product olefin stream from the compressed cracked gas stream, wherein the olefin synthesis plant is configured such that, relative to a conventional olefin synthesis plant, more of the energy and/or the net energy required by the olefin synthesis plant and/or one or more sections thereof, is provided by a non-carbon based and/or renewable energy source and/or electricity.

19 Claims, 8 Drawing Sheets

Related U.S. Application Data

(60) Provisional application No. 62/792,615, filed on Jan. 15, 2019, provisional application No. 62/792,619, filed on Jan. 15, 2019, provisional application No. 62/792,627, filed on Jan. 15, 2019, provisional application No. 62/792,612, filed on Jan. 15, 2019, provisional application No. 62/792,637, filed on Jan. 15, 2019, provisional application No. 62/792,636, filed on Jan. 15, 2019, provisional application No. 62/792,622, filed on Jan. 15, 2019, provisional application No. 62/792,634, filed on Jan. 15, 2019, provisional application No. 62/792,632, filed on Jan. 15, 2019, provisional application No. 62/792,633, filed on Jan. 15, 2019, provisional application No. 62/792,617, filed on Jan. 15, 2019, provisional application No. 62/792,631, filed on Jan. 15, 2019, provisional application No. 62/792,635, filed on Jan. 15, 2019.

(51) Int. Cl.

| | |
|---|---|
| ***B01D 53/26*** | (2006.01) |
| ***B01J 4/00*** | (2006.01) |
| ***B01J 6/00*** | (2006.01) |
| ***B01J 19/24*** | (2006.01) |
| ***C01B 3/12*** | (2006.01) |
| ***C01B 3/34*** | (2006.01) |
| ***C01B 3/48*** | (2006.01) |
| ***C01B 3/56*** | (2006.01) |
| ***C01C 1/02*** | (2006.01) |
| ***C01C 1/04*** | (2006.01) |
| ***C07C 4/00*** | (2006.01) |
| ***C07C 4/02*** | (2006.01) |
| ***C07C 4/04*** | (2006.01) |
| ***C07C 29/132*** | (2006.01) |
| ***C07C 29/152*** | (2006.01) |
| ***F25J 3/02*** | (2006.01) |
| ***H01M 8/04082*** | (2016.01) |
| ***H01M 8/0606*** | (2016.01) |
| ***H01M 8/0612*** | (2016.01) |
| ***H02J 15/20*** | (2026.01) |
| ***H02J 15/50*** | (2026.01) |
| *H01M 8/1007* | (2016.01) |

(52) U.S. Cl.

CPC ............... *B01J 4/008* (2013.01); *B01J 6/008* (2013.01); *B01J 19/0033* (2013.01); *B01J 19/2465* (2013.01); *C01B 3/12* (2013.01); *C01B 3/342* (2013.01); *C01B 3/48* (2013.01); *C01B 3/56* (2013.01); *C01C 1/02* (2013.01); *C01C 1/0417* (2013.01); *C01C 1/0488* (2013.01); *C07C 4/02* (2013.01); *C07C 4/04* (2013.01); *C07C 29/132* (2013.01); *C07C 29/152* (2013.01); *F25J 3/0233* (2013.01); *H01M 8/04201* (2013.01); *H01M 8/0606* (2013.01); *H01M 8/0618* (2013.01); *H02J 15/20* (2026.01); *H02J 15/50* (2026.01); *B01D 2256/16* (2013.01); *B01D 2256/245* (2013.01); *B01J 2219/00051* (2013.01); *B01J 2219/00132* (2013.01); *B01J 2219/00761* (2013.01); *B01J 2219/0871* (2013.01); *C01B 2203/0216* (2013.01); *C01B 2203/0233* (2013.01); *C01B 2203/0238* (2013.01); *C01B 2203/0244* (2013.01); *C01B 2203/0261* (2013.01); *C01B 2203/0283* (2013.01); *C01B 2203/0294* (2013.01); *C01B 2203/04* (2013.01); *C01B 2203/061* (2013.01); *C01B 2203/066* (2013.01); *C01B 2203/068* (2013.01); *C01B 2203/085* (2013.01); *C01B 2203/148* (2013.01); *H01M 8/1007* (2016.02)

(58) Field of Classification Search

CPC ... B01J 4/001; B01J 4/008; B01J 6/008; B01J 2219/00051; B01J 2219/00132; B01J 2219/00761; B01J 2219/0871; B01D 53/047; B01D 53/265; B01D 2256/16; B01D 2256/245; C01B 3/12; C01B 3/34; C01B 3/342; C01B 3/48; C01B 3/56; C01B 2203/0216; C01B 2203/0233; C01B 2203/0238; C01B 2203/0244; C01B 2203/0261; C01B 2203/0283; C01B 2203/0294; C01B 2203/04; C01B 2203/061; C01B 2203/066; C01B 2203/068; C01B 2203/085; C01B 2203/127; C01B 2203/148; C01C 1/02; C01C 1/0417; C01C 1/0488; C07C 1/02; C07C 7/148; C07C 4/02; C07C 4/04; C07C 29/132; C07C 29/1518; C07C 29/152; C07C 29/76; C07C 31/04; C07C 11/02; F25J 3/0233; H01M 8/04201; H01M 8/0606; H01M 8/0612; H01M 8/0618; H01M 8/1007; H02J 15/00; H02J 15/20; H02J 15/50; Y02P 20/133; C07B 61/00; C07B 63/00

See application file for complete search history.

(56) References Cited

U.S. PATENT DOCUMENTS

| | | | |
|---|---|---|---|
| 3,644,100 | A | 2/1972 | Lhonore et al. |
| 3,705,009 | A | 12/1972 | Dougherty |
| 4,140,602 | A | 2/1979 | Lewis et al. |
| 4,158,637 | A | 6/1979 | Jones |
| 4,233,127 | A | 11/1980 | Monahan |
| 4,391,794 | A | 7/1983 | Silberring |
| 4,434,133 | A | 2/1984 | Down et al. |
| 4,684,759 | A | 8/1987 | Lam |
| 5,059,404 | A | 10/1991 | Mansour |
| 5,122,299 | A | 6/1992 | Leblanc |
| 5,180,570 | A | 1/1993 | Lee et al. |
| 5,321,191 | A | 6/1994 | Alagy et al. |
| 5,620,670 | A | 4/1997 | Benham et al. |
| 6,100,303 | A | 8/2000 | Hirotani et al. |
| 6,183,703 | B1 | 2/2001 | Hsu et al. |
| 6,506,510 | B1 | 1/2003 | Sioui et al. |
| 7,288,690 | B2 | 10/2007 | Bellet et al. |
| 7,300,642 | B1 | 11/2007 | Pedersen et al. |
| 2004/0033174 | A1 | 2/2004 | Bruck |
| 2004/0060301 | A1 | 4/2004 | Aceves et al. |
| 2004/0060304 | A1 | 4/2004 | Aceves et al. |
| 2004/0127759 | A1 | 7/2004 | Van Egmond |
| 2005/0271924 | A1 | 12/2005 | Coors et al. |
| 2006/0116543 | A1 | 6/2006 | Bellet |

(56) References Cited

U.S. PATENT DOCUMENTS

| | | | |
|---|---|---|---|
| 2006/0207178 | A1 | 9/2006 | Hsu |
| 2006/0211777 | A1 | 9/2006 | Severinsky |
| 2007/0204512 | A1 | 9/2007 | Self et al. |
| 2008/0156696 | A1 | 7/2008 | Niccum et al. |
| 2011/0042620 | A1 | 2/2011 | Singh et al. |
| 2011/0229780 | A1 | 9/2011 | Kershaw |
| 2012/0055331 | A1 | 3/2012 | Steele |
| 2012/0149788 | A1 | 6/2012 | Ahmed et al. |
| 2012/0186252 | A1 | 7/2012 | Schmidt |
| 2013/0177975 | A1 | 7/2013 | Goetz et al. |
| 2013/0252034 | A1 | 9/2013 | Hu et al. |
| 2014/0194539 | A1 | 7/2014 | Hammad et al. |
| 2015/0129805 | A1 | 5/2015 | Karpenko et al. |
| 2015/0232999 | A1 | 8/2015 | Busskamp et al. |
| 2015/0275108 | A1 | 10/2015 | Gueh |
| 2016/0017800 | A1 | 1/2016 | Simpson |
| 2016/0060537 | A1 | 3/2016 | Hsu |
| 2016/0122194 | A1 | 5/2016 | Markowz et al. |
| 2016/0347908 | A1 | 12/2016 | Muller et al. |
| 2016/0369191 | A1 | 12/2016 | Ward |
| 2017/0137355 | A1 | 5/2017 | Sarsani et al. |
| 2017/0362147 | A1 | 12/2017 | Won et al. |
| 2018/0237555 | A1 | 8/2018 | Buach et al. |
| 2020/0055738 | A1 | 2/2020 | Baratto et al. |
| 2020/0299143 | A1 | 9/2020 | Højlund Nielsen |
| 2020/0406212 | A1 | 12/2020 | Mortensen et al. |
| 2021/0061655 | A1 | 3/2021 | El-Halwagi et al. |
| 2021/0113980 | A1 | 4/2021 | Van Der Ploeg |
| 2021/0261425 | A1 | 8/2021 | Rossi et al. |
| 2021/0301685 | A1 | 9/2021 | Balthasar et al. |
| 2022/0119269 | A1 | 4/2022 | Huckman et al. |

FOREIGN PATENT DOCUMENTS

| | | | |
|---|---|---|---|
| CN | 102753656 | | 10/2012 |
| CN | 103003192 | | 3/2013 |
| CN | 103025649 | | 4/2013 |
| CN | 105209372 | | 12/2015 |
| CN | 105209373 | | 12/2015 |
| CN | 107223114 | | 9/2017 |
| CN | 108368037 | | 8/2018 |
| DE | 102016209155 | | 11/2017 |
| EA | 029413 | | 3/2018 |
| EP | 0539244 | A1 | 4/1993 |
| EP | 2281793 | | 2/2011 |
| EP | 2662327 | | 11/2013 |
| EP | 3249027 | | 11/2017 |
| EP | 3017025 | | 3/2018 |
| FR | 2473032 | | 7/1981 |
| JP | S4614246 | | 4/1971 |
| JP | S54136574 | | 10/1979 |
| JP | S62089634 | | 4/1987 |
| JP | H0565237 | | 3/1993 |
| JP | H05147903 | | 6/1993 |
| JP | AH5222379 | | 8/1993 |
| JP | H05222379 | | 8/1993 |
| JP | AH9235564 | | 9/1997 |
| JP | 2003504485 | | 2/2003 |
| JP | A2004524338 | | 8/2004 |
| JP | A2005515295 | | 5/2005 |
| JP | A2009531529 | | 9/2009 |
| JP | 4585729 | B2 | 11/2010 |
| JP | 2013537042 | A | 9/2013 |
| KR | 2014-0140562 | | 3/2012 |
| RU | 2203214 | | 4/2003 |
| RU | 2005/102272 | | 7/2006 |
| RU | 2501841 | | 12/2013 |
| RU | 2534092 | | 11/2014 |
| RU | 2570659 | | 12/2015 |
| RU | 2617772 | | 4/2017 |
| SU | 823377 | | 4/1981 |
| WO | WO 02/074721 | | 9/2002 |
| WO | WO 03/062352 | | 7/2003 |
| WO | WO 2007117919 | | 10/2007 |
| WO | WO 2008/122399 | | 10/2008 |
| WO | WO 2011/083333 | | 7/2011 |
| WO | WO 2013/124092 | | 8/2013 |
| WO | WO 2016/209508 | | 12/2016 |
| WO | WO 2018/234971 | | 12/2018 |
| WO | WO 2023/202973 | | 10/2023 |
| WO | WO 2023/202974 | | 10/2023 |

OTHER PUBLICATIONS

Bazzanella et al., "Low carbon energy and feedstock for the European chemical industry", pp. 1-168, 2017.

Doyle, "BASF announces four research projects for reducing C02 emissions—News—The Chemical Engineer", pp. 1-14, 2019.

Ekejiuba "Evaluation of the Exact Production Quantity of Nitrogen Fertilizer in Real-Time from any Particular Associated Gas Flare Volume in Nigeria" International Journal of Applied Science and Technology vol. 7, No. 3, Sep. 3, 2017, pp. 87-100.

Extended European Search Report issued in corresponding European Application No. 20740942.6 dated Oct. 18, 2022.

Hobson, et al. "Renewable methanol report" *Methanol Institute*, Dec. 2018, pp. 1-26.

Hydrogen Council "How hydrogen empowers the energy transition" Jan. 2017 https://hydrogencouncil.com/wp-content/uploads/2-17/06/Hydrogen-Council-Vision-Document.pdf.

International Search Report and Written Opinion issued in corresponding International application PCT/US2020/013521 mailed Mar. 31, 2020.

Lewis, Jonathan "Fuels Without Carbon Prospects and the Pathway Forward for Zero-Carbon Hydrogen and Ammonia Fuels" Dec. 2018 https://www.catf.us.resouce/fuels-ithout-carbon/.

Max Appl. "Ammonia, 3. Production Plants." *Ullman's Encyclopedia of Industrial Chemistry*, Wiley-VCH, 2012, pp. 227-261.

Mortensen, et al. "Direct Hysteresis Heating of Catalytically Active Ni-Co Nanoparticles as Steam Reforming Catalyst" Industrial & Engineering Chemistry Research vol. 56, No. 47, Nov. 15, 2017, pp. 14006-14013.

Office Action issued in corresponding Saudi Application No. 521422542 dated Dec. 25, 2022.

Office Action issued in corresponding Chinese Application No. 202080021257.9, dated Sep. 15, 2022.

Office Action issued in corresponding Japanese Application No. 2021540821, dated Sep. 26, 2023.

Office Action issued in corresponding Russian Application No. 2021123908 dated Jun. 7, 2023.

Pattabathula, et al. "Introduction to Ammonia Production" Chemical Engineering Progress Sep. 2016, pp. 69-75.

Pre-Appeal Examination Report issued in corresponding Japanese Application No. 2021540821, dated Nov. 12, 2024. (English Translation provided).

Third Party Observation filed with the European Patent Office dated Aug. 28, 2024 in corresponding European Patent Application No. 20740942.6.

Third-Party Submission of Information filed with the Japan Patent Office on Jul. 31, 2024 in corresponding Japanese Application No. 2021-540821.

Third-Party Submission of Information filed with the Korean Patent Office on Jul. 4, 2024 in corresponding Korean Application No. 10-2021-7024976.

Wang et al., "Greening Ammonia toward the Solar Ammonia Refinery" Joule, 2, Jun. 20, 2018, pp. 1055-1074.

Weinian, Feng Et al. "Encyclopedia of Chemical Engineering" (vol. 3 "Tool Materials—Power Generation Doa fa", pp. 407-408, Chemical Industry Press, Mar. 1993. (no translation available).

Wismann, et al., "Electrified methane reforming: A compact approach to greener industrial hydrogen production" *Science*, vol. 364, No. 6442, May 24, 2019, pp. 756-759.

Zimmermann et al., "Ethylene" In: Ullmann's Encyclopedia of Wiley-VCH Industrial Chemistry, 2009.

Rafiqul et al., "Energy efficiency improvements in ammonia production—perspectives and uncertainties." *Energy*, vol. 30, 2005, pp. 2487-2504.

(56) References Cited

OTHER PUBLICATIONS

Office Action issued in corresponding Chinese Application No. 202311659620.1, dated Mar. 25, 2026 (Machine Translation provided).
Office Action issued in corresponding Chinese Application No. 202311659620.1, dated Sep. 29, 2025 (Machine Translation provided).

Comparative Example 1

Example 2

Example 3

Example 2, 4 and 5

USE OF RENEWABLE ENERGY IN OLEFIN SYNTHESIS

CROSS-REFERENCE TO RELATED APPLICATIONS

This application is a continuation of U.S. application Ser. No. 17/310,072, filed Jul. 15, 2021, which is a national phase application under 35 U.S.C. § 371 of International Application No. PCT/US2020/013521 filed Jan. 14, 2020, which claims the benefit of priority of U.S. Provisional Patent Application No. 62/792,612 filed Jan. 15, 2019, U.S. Provisional Patent Application No. 62/792,615 filed Jan. 15, 2019, U.S. Provisional Patent Application No. 62/792,617 filed Jan. 15, 2019, U.S. Provisional Patent Application No. 62/792,619 filed Jan. 15, 2019, U.S. Provisional Patent Application No. 62/792,622 filed Jan. 15, 2019, U.S. Provisional Patent Application No. 62/792,627 filed Jan. 15, 2019, U.S. Provisional Patent Application No. 62/792,631 filed Jan. 15, 2019, U.S. Provisional Patent Application No. 62/792,632 filed Jan. 15, 2019, U.S. Provisional Patent Application No. 62/792,633 filed Jan. 15, 2019, U.S. Provisional Patent Application No. 62/792,634 filed Jan. 15, 2019, U.S. Provisional Patent Application No. 62/792,635 filed Jan. 15, 2019, U.S. Provisional Patent Application No. 62/792,636 filed Jan. 15, 2019, U.S. Provisional Patent Application No. 62/792,637 filed Jan. 15, 2019, all of which are hereby incorporated by reference in their entirety.

TECHNICAL FIELD

The present disclosure relates to the use of renewable energy in the synthesis of olefins; more particularly, the present disclosure relates to the electrification of an olefin synthesis plant; still more particularly, the present disclosure relates to a reduction in environmental emissions, such as carbon dioxide, by reducing the combustion of hydrocarbons (e.g., natural gas/fossil fuels) for fuel in an olefins synthesis plant.

BACKGROUND

Chemical synthesis plants are utilized to provide a variety of chemicals. Often, a dedicated fuel is burned or 'combusted' to provide heat of reaction for chemical synthesis, energy to heat one or more process streams, energy to vaporize liquids (e.g., boil water used as a diluent), energy to do work (e.g., drive a compressor or pump), or energy for other process operations throughout the chemical synthesis plant. Such burning or combustion of fuels results in the production of flue gases, which can be harmful to the environment, and also results in a loss of energy efficiency of the process. Likewise, steam is often conventionally utilized as a plant-wide heat and/or energy transfer fluid within chemical synthesis plants. The steam utilized for the heat and/or energy transfer is often produced via the combustion of a fuel, resulting in the production of additional flue gas and further energy efficiency losses during the chemical synthesis. Additionally, the use of a material that could otherwise be utilized as a reactant for combustion as a fuel also reduces an amount of the desired chemical product produced in the chemical synthesis plant from a given amount of the material. Accordingly, a need exists for enhanced systems and methods of chemical synthesis whereby an amount of fuels, especially fossil fuels, burned to provide energy is reduced or eliminated. Desirably, such systems and methods also provide for an increase in energy efficiency and/or a decrease in emissions, such as emissions of greenhouse gases (GHG), by the chemical synthesis plant.

SUMMARY

Herein disclosed is an olefin synthesis plant for the production of light olefins, the olefin synthesis plant comprising: a feed pretreatment section configured to pretreat a feed stream; a pyrolysis section comprising one or more pyrolysis reactors configured to crack hydrocarbons in the feed stream in the presence of a diluent to produce a cracked gas stream; a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that, relative to a conventional olefin synthesis plant, more of the energy and/or the net energy required by the olefin synthesis plant, the feed pretreatment section, the pyrolysis section, the primary fractionation and compression section, the product separation section, or a combination thereof, is provided by a non-carbon based energy source, a renewable energy source and/or electricity.

Also disclosed herein is an olefin synthesis plant for the production of light olefins, the olefin synthesis plant comprising: a feed pretreatment section configured to pretreat a feed stream; a pyrolysis section comprising one or more pyrolysis reactors configured to crack hydrocarbons in the feed stream in the presence of a diluent to produce a cracked gas stream; a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that a majority of the process energy and/or the net process energy required by the olefin synthesis plant, the feed pretreatment section, the pyrolysis section, the primary fractionation section, the product separation section, or a combination thereof, is provided by electricity.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
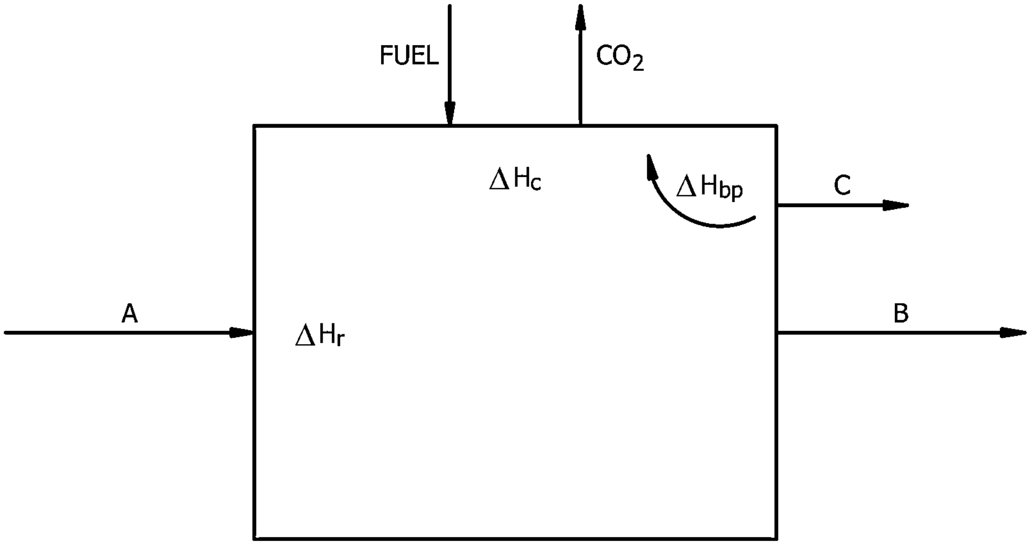
FIG. 1 (Prior Art)
FIG. 1 shows a conceptual diagram of a typical prior art chemical process.

It should be understood at the outset that although an illustrative implementation of one or more embodiments are provided below, the disclosed compositions, methods, and/or products may be implemented using any number of techniques, whether currently known or not yet in existence. The disclosure should in no way be limited to the illustrative implementations, drawings, and techniques illustrated hereinbelow, including the exemplary designs and implementations illustrated and described herein, but may be modified within the scope of the appended claims along with their full scope of equivalents.

While the following terms are believed to be well understood by one of ordinary skill in the art, the following definitions are set forth to facilitate explanation of the presently disclosed subject matter. Unless defined otherwise, all technical and scientific terms used herein have the same meaning as commonly understood to one of ordinary skill in the art to which the presently disclosed subject matter belongs.

As utilized herein, an 'intermittent energy source' or 'IES' is any source of energy that is not continuously available for conversion into electricity and outside direct control because the used energy cannot be stored or is economically undesirable. The availability of the intermittent energy source may be predictable or non-predictable. A renewable intermittent energy source is an intermittent energy source that is also a source of renewable energy, as defined hereinbelow. 'Intermittent electricity' refers to electricity produced from an IES.

As utilized herein, 'renewable energy' and 'non-fossil based energy ($E_{NF}$)' includes energy derived from a sustainable energy source that is replaced rapidly by a natural, ongoing process, and nuclear energy. Accordingly, the terms 'renewable energy' and 'non-fossil based energy ($E_{NF}$)' refer to energy derived from a non-fossil fuel based energy source (e.g., energy not produced via the combustion of a fossil fuel such as coal or natural gas), while 'non-renewable' or 'fossil based energy ($E_F$)' is energy derived from a fossil fuel-based energy source (e.g., energy produced via the combustion of a fossil fuel). Fossil fuels are natural fuels, such as coal or gas, formed in the geological past from the remains of living organisms. Accordingly, as utilized herein, 'renewable' and 'non-fossil based energy ($E_{NF}$)' include, without limitation, wind, solar power, water flow/movement, or biomass, that is not depleted when used, as opposed to 'non-renewable' energy from a source, such as fossil fuels, that is depleted when used. Renewable energy thus excludes fossil fuel based energy ($E_F$) and includes biofuels.

As utilized herein, 'non-carbon based energy ($E_{NC}$)' is energy from a non-carbon based energy source (e.g., energy not produced via the combustion of a carbon-based fuel such as a hydrocarbon), while carbon based energy ($E_C$) is energy from a carbon-based energy source (e.g., energy produced via the combustion of a carbon-based fuel such as a hydrocarbon). Nuclear energy is considered herein a renewable, non-fossil ($E_{NF}$) based energy and a non-carbon based energy ($E_{NC}$). Carbon-based energy ($E_C$) can thus be renewable (e.g., non-fossil fuel based) or non-renewable (e.g., fossil fuel-based). For example, various carbon-based biofuels are herein considered renewable, carbon-based energy sources.

As utilized herein, 'renewable electricity' indicates electricity produced from a renewable energy source, while 'non-renewable electricity' is electricity produced from a non-renewable energy source. As utilized herein 'non-carbon based electricity' indicates electricity produced from a non-carbon based energy source, while 'carbon-based electricity' is electricity produced from a carbon-based energy source.

For example, in embodiments, renewable electricity and/or heat throughout the herein-disclosed olefin synthesis plant can be provided by the combustion of renewable hydrocarbons that come from renewable (e.g., biological) sources. For example, renewable electricity can, in embodiments, be produced via the combustion of an $E_{NF}/E_C$ energy source comprising methane produced in a digester fed with agricultural wastes. Likewise, in embodiments, an $E_{NF}/E_C$ energy source comprising synthesis gas produced using short cycle carbon waste materials can be utilized as a fuel (e.g., combusted to produce renewable electricity and/or heat). Desirably, the carbon dioxide generated by such combustion is recaptured (e.g., by the growth of a new crop).

As utilized herein, 'externally' combusting a fuel refers to combusting a fuel outside of a reactor, e.g., in a furnace. Combustion as a part of the primary reaction (e.g., combustion which takes place with reforming in autothermal reforming (ATR)) would not be considered 'externally' combusting. As utilized herein, a 'dedicated' fuel is a fuel or portion of a feed stream introduced solely to provide fuel value (e.g., combustion heat) and not be converted into product.

As utilized herein, 'heat transfer steam ($S_{HT}$)' indicates steam produced solely or primarily as an energy or heat transfer medium (e.g., steam not utilized as a diluent and/or reactant).

As utilized herein, 'net' heat input or removal refers to heat input or removal that results in primary energy consumption, e.g., heat input or removal not provided from another section or stream of the plant, e.g., not provided via heat exchange with another process stream. Similarly, 'net' energy refers to energy that results in primary energy consumption, e.g., energy not provided from another section or stream of the plant, e.g., thermal energy not provided via heat exchange with another process stream.

As utilized herein, 'powering' indicates supplying with mechanical and/or electrical energy.

As utilized herein, 'heating' indicates supplying with thermal energy. As utilized herein 'cooling' indicates the removal of thermal energy therefrom. As utilized herein, 'direct' heating or cooling refer to heating or cooling without the use of a heat transfer medium/fluid: 'indirect' heating or cooling refer to heating or cooling via a heat transfer medium/fluid.

As utilized herein, 'most' or 'a majority' indicates more than 50% or more than half.

As utilized herein, a 'desired' parameter (e.g., desired temperature) may refer to an intended or target value for the parameter, for example a predetermined value such as a set-point value used for process control.

Amount of electricity consumed: References to consumption of electricity may refer to a rate at which electricity is used (e.g., in MW), as measured at a particular location. For example, a rate may be calculated at the boundary of each electrified furnace or at an overall olefin synthesis plant boundary. This calculation may consider all electricity used within that location.

Flue gas: A mixture of gases that may be produced by the burning of fuel or other materials in a power station and/or industrial plant, where the mixture of gases may be extracted via ducts.

Flue gas heat recovery: Flue gas heat recovery may refer to the extraction of useful thermal energy from hot flue gases, for example by passing said hot flue gas over one or more heat exchangers to raise the temperature of a cooler process fluid and/or change the phase of said fluid (e.g., boil water to raise steam). Any energy remaining in the flue gas after any flue gas heat recovery may be termed flue gas (energy) loss. A flue gas heat recovery section may be the equipment and corresponding location of said equipment used to recover flue gas heat. A lack of flue gas heat recovery section may mean there is no equipment or area where heat is recovered from hot flue gases.

Convection section: A convection section may be a portion of a furnace (e.g., steam cracking furnace or reforming furnace) where heat is recovered from hot flue gases by convective heat transfer. A lack of convection section may mean that there is no equipment or area where heat is recovered by convective heat transfer from hot flue gases.

"Steam-free" or "Substantially Steam-free": "Steam free" may refer to a process where steam is not used to transfer energy from one process operation to another, or to bring energy into the process from outside. "Substantially steam-free" may mean that the use of steam to transfer energy from one process operation to another or to bring energy into the process from outside has been minimized such that the sum of all energy transfers using steam amount to less than approximately 10%, approximately 20%, or approximately 30% of the net energy provided. Steam used as a reactant, a diluent, obtained as a product, or directly mixed with a process stream may be termed "process steam" and is not included in this definition.

Primary energy transfer medium: A primary energy transfer medium may be a substance that is used to move energy in the form of thermal energy from one process operation to another, or to bring energy into a process. Note that a substance may serve more than one purpose in a process such as acting as a reactant or reaction diluent whilst also acting as a medium to transfer heat from one process operation to another. In such instances, the use of steam as reactant or diluent may be considered primary and the effect of also transferring heat may be considered secondary.

Resistive heating: Resistive heating may be heating by means of passing electric current through resistive units.

Inductive heating: Induction heating may be a process of heating an electrically conducting object (usually a metal) by electromagnetic induction.

Radiant heating: Radiant heating may be a process of heating an object via radiation from one or more hotter objects.

Externally combusting: Externally combusting may mean burning fuel to generate heat and transferring this heat to a process fluid across a surface (e.g., a tube wall) such that combustion products do not mix with the process fluid.

Thermoelectric device: A thermoelectric device may be a device for the direct conversion of temperature differences to electric voltage (or vice versa) across a thermocouple.

Isothermal operation: Isothermal operations may be operations at a constant temperature. Isothermal operation can keep temperature within 0.5%, 1%, 2%, 3%, 4%, 5% up to 10% of the predetermined operation temperature.

Convective heat transfer: Convective heat transfer may be the movement of heat from one place to another by the movement of a fluid or fluids.

Although the majority of the above definitions are substantially as understood by those of skill in the art, one or more of the above definitions can be defined hereinabove in a manner differing from the meaning as ordinarily understood by those of skill in the art, due to the particular description herein of the presently disclosed subject matter.

FIG. 1 shows a conceptual diagram of a typical traditional chemical process. The goal of this process is to convert feed A into product B, although often some byproducts (indicated as stream C) are also produced.

The unit operations used to effect this transformation require significant amounts of energy. Conventionally, this energy is primarily supplied by burning a fuel, often natural gas, to generate heat, denoted in FIG. 1 as $\Delta H_c$ (e.g., heat of combustion). This results in the undesirable production and emission of carbon dioxide ($CO_2$). Additional energy may be supplied by the heat of reaction, $\Delta H_r$, if the reaction is exothermic; if the reaction is endothermic, an additional amount of energy equal to $\Delta H_r$ will need to be added. The total energy balance may also be affected if some byproducts are burned to produce energy, indicated as $\Delta H_{bp}$. However, many chemical processes, even those involving exothermic reactions, are net energy consumers and thus require an external source of energy (typically provided by a hydrocarbon fuel(s)) to provide net process energy.

Electricity is usually only a small external input into most chemical production processes. Internal electrical requirements, such as for lighting or control, are usually so small as to be negligible, and in those few processes which require large amounts of electricity, for example, electrochemical reactors (e.g., the chlor-alkali process to make chlorine ($Cl_2$) and sodium hydroxide (NaOH)), this electricity is commonly generated within the plant boundaries by the combustion of hydrocarbons, and, even when not generated within the plant boundaries, if the electricity is obtained by the combustion of hydrocarbons rather than renewably, such use of electricity is equivalent in terms of energy efficiency and $CO_2$ emissions to on-site production of the electricity via hydrocarbon combustion.

Within most chemical production processes, energy consumption can conveniently be divided into three main categories. In the first such broad category, referred to herein as first category C1, heat is supplied directly as thermal energy by the combustion of a fuel (e.g., natural gas/fossil fuels) in a furnace. (As utilized, here. 'directly' indicates the absence of an intermediate heat transfer medium, such as steam.) These furnaces are often operated at high temperature and require large heat fluxes. The energy efficiency of such furnaces is limited by the heat losses in the furnace flue gas. Even where these heat losses are minimized by the cooling of the flue gas to recover energy, for example to generate steam or provide process heating, the conversion of the chemical energy contained in the fuel to usable thermal energy generally does not exceed 85 to 90%, even with substantial investment and loss of design and operating flexibility.

The second broad category, referred to herein as second category C2, of energy consumption in chemical processes comprises the heating of various chemical streams, primarily either to raise the temperature thereof to a predetermined reaction temperature or to provide energy for separations, most commonly distillation. Although some of this heat can be obtained by exchange with other chemical streams, it is most typically provided either by steam generated directly by the combustion of hydrocarbon fuels (e.g., natural gas/fossil fuels) or by heat transfer from the flue gas from high-temperature furnaces (e.g., from category C1). Most modern chemical processes include a relatively complicated steam system (or other heat transfer fluid system which will generically be referred to herein for simplicity as a steam heat transfer system) to move energy from where it is in excess to where it is needed. This steam system may include multiple pressure levels of steam to provide heat at different temperatures, as well as a steam and condensate recovery system, and is subject to corrosion, fouling, and other operational difficulties, including water treatment and contaminated condensate disposal. The fraction of the energy contained in the steam that can be used to heat process streams is generally limited to 90 to 95% by practical constraints on heat transfer, steam condensation, and boiler water recycle. If the steam was generated by an on-purpose external boiler, at most 80 to 85% of the chemical energy contained in the fuel will be used as heat by the chemical process, since an additional 10 to 15% or more will be lost to flue gas as in first category C1.

The third major category, referred to herein as third category C3, of energy usage in chemical processes is energy utilized to perform mechanical work. This work is primarily utilized for pressurizing and moving fluids from one place to another, and is used to drive rotating equipment such as pumps, compressors, and fans. This third category C3 also includes refrigeration equipment, since it is primarily powered by compression. In most chemical facilities, the energy for this work is provided by steam, obtained either by heat transfer with hot process streams, by heat transfer with partially-cooled flue gas streams from a furnace (e.g., in the convection section) in category C1, or directly from the combustion of hydrocarbons (e.g., natural gas/fossil fuels) in an on-purpose external boiler. Because of limitations on the conversion of thermal energy to mechanical work, the energy efficiency of these uses relative to the contained chemical energy of the hydrocarbons used as fuel is low, typically only 25 to 40%.

It has been unexpectedly discovered that using electricity (e.g., renewable and/or non-renewable electricity) to replace energy obtained from a hydrocarbon fuel in a chemical process can improve the process by increasing overall energy efficiency, while decreasing carbon dioxide emissions. In some cases, using electricity (e.g., renewable and/or non-renewable electricity) to replace energy obtained from a hydrocarbon fuel in a chemical process can also improve reliability and operability, decrease emissions of, for example, NOx, SOx, CO, and/or volatile organic compounds, and/or decrease production costs (e.g., if low-cost electricity is available).

According to embodiments of this disclosure, heat conventionally supplied as thermal energy by the combustion of a fuel (e.g., natural gas/fossil fuels) in a furnace and/or other heating in first category C1 is replaced by electrical heating. Electrical heat, electrical heating, generating heat electrically, electrical heater apparatus, and the like refer to the conversion of electricity into thermal energy available to be applied to a fluid. Such electrical heating includes, without limitation, heating by impedance (e.g., where electricity flows through a conduit carrying the fluid to be heated), heating via ohmic heating, plasma, electric arc, radio frequency (RF), infrared (IR), UV, and/or microwaves, heating by passage over a resistively heated element, heating by radiation from an electrically-heated element, heating by induction (e.g., an oscillating magnetic field), heating by mechanical means (e.g. compression) driven by electricity, heating via heat pump, heating by passing a relatively hot inert gas or another medium over tubes containing a fluid to be heated, wherein the hot inert gas or the another medium is heated electrically, or heating by some combination of these or the like.

According to embodiments of this disclosure, the utilization of steam (or another heat transfer fluid) as in second category C2 is eliminated and/or any steam (or other fluid) utilized solely as an intermediate heat transfer medium is electrically produced or heated (e.g., via electrical heating of water).

According to embodiments of this disclosure, conventional rotating equipment (e.g., steam turbines) utilized in third category C3 is replaced with electrically driven apparatus. According to embodiments of this disclosure, heat removal in third category C3 is replaced by electrically-powered heat removal, e.g., cooling and/or refrigeration. Electrical cooling, electrical coolers, removing heat electrically, electrical cooling or refrigeration apparatus, and the like refer to the removal of thermal energy from a fluid. Such electrical cooling includes, without limitation, cooling by electrically powered apparatus. For example, and without limitation, electrical cooling can be provided by powering a refrigeration cycle with electricity, wherein a refrigerant is compressed by an electrically powered compressor. As another example, electrical cooling can be provided by powering a cooling fan that blows air, wherein the air cools a process fluid or element. In embodiments, electrical heating and cooling can be effected by any electrical source.

Figure 2:
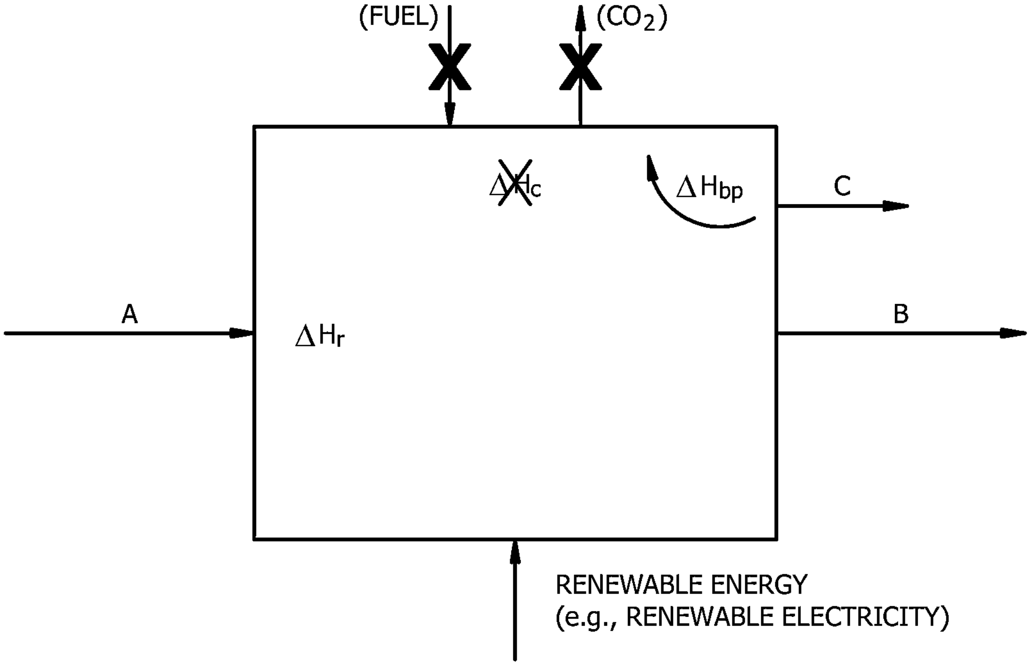
FIG. 2 shows a conceptual diagram of a chemical process powered by renewable energy, according to embodiments of this disclosure.

FIG. 2 is a schematic of a chemical process powered by renewable energy, according to embodiments of this disclosure. As shown in FIG. 2, a process driven by renewable energy can, in embodiments, appear similar to a conventional chemical process. However, a portion, a majority, or, in some cases, substantially all of the energy input supplied by fuel can be replaced by renewable energy and/or by renewable electricity. Such replacement of fuel input by non-carbon based energy, renewable energy, and/or renewable electricity will allow for a significant decrease in $CO_2$ emissions, in embodiments. In embodiments, any available form of renewable energy can be employed. However, the gains may be greatest if renewable electricity is utilized. The renewable energy can be obtained from, for example and without limitation, solar power, wind power, or hydroelectric power. Other types of renewable energy can also be applied in chemical plants according to embodiments of this disclosure. For example, in embodiments, concentrated solar power, geothermal energy, and/or the use of direct solar heating can be used to provide thermal energy and to decrease $CO_2$ emissions.

One of the main advantages to supplying needed energy via (e.g., renewable) electricity can be that the energy efficiency of the process will increase. Table 1 shows the energy efficiency of unit operations exemplifying the three categories of energy use in a chemical plant described above as C1, C2, and C3. It can be seen from Table 1 that the efficiency of each of the three categories of energy consumption is greater when electrical power is used. The gain can be greatest when steam drives for rotating equipment are replaced, according to embodiments of this disclosure, with electrical motors (as in third category C3, discussed hereinabove), which can operate with as much as three times the energy efficiency of steam drives. These gains are only realized when the electricity is derived from non-carbon based renewable sources, since the generation of electricity from carbon-based fuel combustion is only 30 to 45% energy efficient. Energy efficiency gains when using renewable electricity for heating applications (as in first category C1 and second category C2, discussed hereinabove) are smaller, but still significant. The net result is that less total energy will be used if renewable energy is used in place of carbon-based fuels (e.g., natural gas or other hydrocarbons).

TABLE 1

Energy Efficiency of Unit Operations

| Use | Efficiency from Hydrocarbon Combustion | Efficiency from Electricity According to This Disclosure |
|---|---|---|
| C1: Direct Heating | up to 80-90% | 95+% |
| C2: Heating with Steam | up to 80-95% | 95+% |
| C3: Rotating Equipment | 25-40% | 90-95% |

According to this disclosure, non-carbon based energy, renewable energy, and/or electricity (e.g., from renewable and/or non-renewable sources) can be utilized rather than conventional energy sources in categories C1, C2, and/or C3 described hereinabove. In embodiments, electrification is utilized for a majority of or substantially all utilities. In embodiments, electrification is utilized for a majority of or substantially all unit operations. In embodiments, electrification is utilized for a majority of or substantially all utilities and unit operations. In embodiments, electrification is utilized for a majority of or substantially all process applications, engines, cooling and/or heating (e.g., electrically driven heat pumps, refrigeration, electrical heating), radiation, storage systems, or a combination thereof.

In embodiments, the non-carbon based and/or renewable energy source comprises wind, solar, geothermal, hydroelectric, nuclear, tide, wave, ocean thermal gradient power, pressure-retarded osmosis, or a combination thereof. In embodiments, the non-carbon based energy source comprises hydrogen. In embodiments, electricity for electrification as described herein is produced from such a renewable and/or non-carbon based energy source. In embodiments, some or all of the electricity is from a non-renewable and/or carbon-based source, such as, without limitation, combustion of hydrocarbons (e.g., renewable or non-renewable hydrocarbons), coal, or hydrogen derived from hydrocarbons (e.g., renewable or non-renewable hydrocarbons).

The majority of the $CO_2$ emitted from most chemical plants is a result of fossil fuel combustion to provide energy for the plant. An additional benefit of using renewable energy in chemical synthesis as per embodiments of this disclosure is that the amount of greenhouse gases emitted will be significantly (e.g., by greater than or equal to at least 5, 10, 20, 30, 40, 50, 60, 70, 80, 90, or 100%) reduced relative to an equivalent conventional chemical synthesis plant or method in which hydrocarbons and/or fossil fuel(s) may be combusted. The burning of hydrocarbons (e.g., natural gas, methane) to generate energy results in the production of carbon dioxide ($CO_2$); this production can be reduced or avoided by the use of renewable energy according to embodiments of this disclosure. In embodiments of this disclosure, the amount of $CO_2$ produced per ton of product produced is reduced to less than or equal to about 1.6, 1.5, 1.4, 1.3, 1.2, 1.1, 1.0, 0.75, 0.5, 0.3, 0.25, 0.2, 0.1, 0.05, or 0 tons $CO_2$ per ton chemical product (e.g., olefin(s)). Furthermore, in embodiments of this disclosure, the use of renewable energy frees up these hydrocarbons (e.g., natural gas, methane) typically burned for fuel for use as a chemical feedstock (e.g., to make methanol), which is a higher value use.

The use of renewable electricity in the production of chemicals can also lead to operational advantages. For example, in embodiments, electric power can be utilized to provide a more accurate and tunable input of heat, for example to control the temperature profile along a reactor or to change the temperature of specific trays in a distillation column. In embodiments, the use of electric heating in a reaction section (e.g., in a pyrolysis reaction section) leads to better controlled decoking and/or faster decoking. Without limitation, other examples include the use of electric powered refrigeration units to increase the efficiency of separations, and the replacement of inefficient stand-by gas-fired boilers with quick-acting on-demand electrical heaters and steam generators and for other utility uses. The use of electricity may also allow for significant operational advantages during start-up or shut-down, or to respond to process variability. In general, electricity as an energy source can be applied in specific locations and in precise and tunable amounts with a rapid response to process changes, leading to a variety of advantages over the use of thermal/combustion energy.

The use of renewable electricity according to embodiments of this disclosure can also increase the energy efficiency of utilities that supply energy to more than one chemical plant (e.g., an olefin synthesis plant and a nearby ammonia synthesis plant or an olefin synthesis plant and a nearby methanol synthesis plant). For example, if the compressors in an air separation unit that provides oxygen and nitrogen to several different production facilities are powered with renewable electricity, significant energy gains can be achieved relative to supplying this power with steam derived from the combustion of natural gas.

Energy recovery may be provided, in embodiments, via high temperature heat pumps or vapor recompression. The plant may further comprise heat and/or energy storage, for example, for use when an intermittent energy source (IES) is utilized. In embodiments, waste heat can be upgraded to usable temperature levels via electrically driven heat pumps. In other embodiments, energy can be recovered as electricity when process stream pressures are reduced by using a power-generating turbine instead of a control valve. In other embodiments, energy can be recovered as electricity using thermoelectric devices.

The use of renewable electricity to replace natural gas or other hydrocarbons as a source of energy, according to embodiments of this disclosure, can be done as part of a retrofit of an existing chemical process (e.g., an existing olefin synthesis plant) or as an integral component of the design of a new chemical plant (e.g., a new olefin synthesis plant). In a retrofit, opportunities for using renewable energy can depend on elements of the existing design, such as the steam system; in a retrofit, careful examination of the entire energy balance and steam system will be required, as electrifying individual pieces of equipment without regard to these considerations may result in energy inefficiencies. In embodiments, as seen in Table 1, the highest efficiency gains are achieved by replacing steam drives for rotating equipment (e.g., in third category C3) with electric motors. However, differing objectives may lead to different choices in partial electrification; in embodiments, in some instances greater $CO_2$ reductions at the expense of smaller increases in energy efficiency may sometimes be realized by first replacing hydrocarbon-fired furnaces (e.g., in first category C1). In embodiments, if thermal energy and/or steam are obtained from more than one hydrocarbon source, the most advantageous operation can be achieved by eliminating the most expensive and/or polluting fuel sources first. How much renewable energy can be included and to what extent existing fuel consumption and carbon dioxide ($CO_2$) emissions can be decreased can vary depending on the application, and will be within the skill of those of skill in the art upon reading this disclosure.

In embodiments, planning for the use of renewable energy in the design of a grass-roots chemical facility (e.g., a grass-roots olefin synthesis plant) can allow for more significant opportunities for better energy efficiency and lower $CO_2$ emissions. In embodiments, powering all rotating equipment (e.g., in third category C3) with electricity is utilized to realize large gains in energy efficiency. In embodiments, substantially all (or a majority, or greater than 40, 50, 60, 70, 80, or 90%) electric heating (e.g., in first category C1 and/or second category C2) is utilized, and the inefficiencies due to the loss of heat in flue gas are substantially reduced or even avoided. In embodiments, the use of steam generated via the combustion of a fossil fuel (e.g., in second category C2) can be minimized or avoided altogether. In embodiments, a change in catalyst and/or a modification of reactor operating conditions is utilized to allow for less heat generation in a reactor and/or the production of fewer byproducts that are burned. In embodiments, a plant (e.g., olefin synthesis plant) design based on the use of renewable electricity allows for enhanced optimization of separations operations, since the relative costs of compression and refrigeration are changed via utilization of renewable electricity as per this disclosure. Such enhanced separations can, in embodiments, also allow for further capture of minor byproducts from vent streams, freeing these minor products up for further use as feedstocks or products. Furthermore, the use of low-cost electricity, according to embodiments of this disclosure, may allow for the introduction of novel technologies such as, without limitation, hybrid gas and electric heaters, variable speed compressor drives, distributed refrigeration, heat pumps, improved distillation columns, passive solar heating of fluids, precise control of reactor temperature profiles, new materials of construction, and quench or cooling using electrically refrigerated diluents. If the cost of electricity is sufficiently low, utilization of such electricity as taught herein may favor the introduction of new electrochemical processes. For new construction, it may be less capital intensive to drive processes electrically, due, for example, to the lack of a (e.g., plant-wide) steam distribution system.

According to embodiments of this disclosure, non-carbon based energy, renewable energy, and/or electricity (renewable, non-renewable, carbon-based, and/or non-carbon based electricity) can be used in the production of nearly every chemical, including but not limited to methanol, ammonia, olefins (e.g., ethylene, propylene), aromatics, glycols, and polymers. Non-carbon based energy, renewable energy, and/or electricity can also be used, in embodiments, in the preparation of feedstocks for chemicals and for fuels production, such as in methyl tert-butyl ether (MTBE) synthesis, cracking, isomerization, and reforming. In such embodiments, some (e.g., at least about 10, 20, 30, 40, or 50%), a majority (e.g., at least about 50, 60, 70, 80, 90, or 95%), or all (e.g., about 100%) of the heating throughout the plant/process or a section thereof can be provided by electrical heating and/or some (e.g., at least about 10, 20, 30, 40, or 50%), a majority (e.g., at least about 50, 60, 70, 80, 90, or 95%), or all (e.g., about 100%) of the cooling throughout the plant/process or a section thereof can be provided by electrical cooling as described hereinabove. Disclosed hereinbelow is the use of renewable energy, non-carbon based energy, and/or electricity in olefin synthesis (e.g., steam cracking) applications.

The disclosures of U.S. Provisional Patent Application Nos. 62/792,612 and 62/792,615, entitled Use of Renewable Energy in Olefin Synthesis, U.S. Provisional Patent Application Nos. 62/792,617 and 62/792,619, entitled Use of Renewable Energy in Ammonia Synthesis, U.S. Provisional Patent Application Nos. 62/792,622 and 62/792,627, entitled Use of Renewable Energy in Methanol Synthesis, and U.S. Provisional Patent Application Nos. 62/792,631, 62/792,632, 62/792,633, 62/792,634, and 62/792,635, entitled Use of Renewable Energy in the Production of Chemicals, which are being filed on Jan. 15, 2019, are hereby incorporated herein for purposes not contrary to this disclosure.

This disclosure describes an olefin synthesis plant for producing light olefins (e.g., ethylene, propylene, butylenes, butadiene) configured such that a majority of the net energy required by one or more sections, units, or groups of like units or unit operations of the olefin synthesis plant is provided by non-carbon based energy ($E_{NC}$) from a non-carbon based energy source (e.g., not produced via the combustion of a carbon-based fuel such as a hydrocarbon), from renewable energy (e.g., from non-fossil fuel derived energy ($E_{NF}$)), and/or from electricity. The $E_{NC}$ or $E_{NF}$ source may, in embodiments, comprise, primarily comprise, consist essentially of, or consist of electricity. The $E_{NC}$ or $E_{NF}$ source may, in embodiments, comprise, primarily comprise, consist essentially of, or consist of renewable electricity. In embodiments a portion (e.g., greater than or equal to about 5, 10, 20, 30, 40, 50), a majority (e.g., greater than or equal to about 50, 60, 70, 80, 90, or 95%), or all (e.g., about 100%) of the net energy needed by the overall olefin synthesis plant, a section of the plant (e.g., a feed pretreatment section, a pyrolysis reaction section, a primary fractionation and compression section, and/or a product fractionation section), a group of like units (e.g., compressors, power providing units, heating units, reboilers, cooling units, refrigeration units, separators, distillation/fractionation columns, furnaces/pyrolysis reactors, reboilers), or unit operations (e.g., compression, powering, cracking operations, separations, heating operations, cooling operations) of the plant, or a combination thereof is provided by electricity, renewable energy (e.g., non-fossil fuel derived energy ($E_{NF}$)), and/or non-carbon based energy ($E_{NC}$). In embodiments, electricity is provided from a renewable energy source, such as, without limitation, wind (e.g., via wind turbines), solar (e.g., photovoltaic (PV) panels or solar thermal), hydroelectric, wave, geothermal, nuclear, tide, biomass combustion with associated capture of $CO_2$ in replacement crops, or a combination thereof. In embodiments a portion (e.g., greater than or equal to about 5, 10, 20, 30, 40, 50), a majority (e.g., greater than or equal to about 50, 60, 70, 80, 90, or 95%), or all (e.g., about 100%) of the electricity, renewable energy (e.g., non-fossil fuel derived energy ($E_{NF}$)), or non-carbon based energy ($E_{NC}$) needed by the overall olefin synthesis plant, a section of the plant (e.g., a feed pretreatment section, a pyrolysis reaction section, a primary fractionation and compression section, and/or a product fractionation section), a unit or a group of like units (e.g., compressors, power providing units, heating units, reboilers, cooling units/refrigeration units, separators, distillation/fractionation columns, furnaces/pyrolysis reactors, reboilers) or unit operations (e.g., compressing, powering, cracking operations, separations, heating operations, cooling operations) of the olefin synthesis plant, or a combination thereof, and conventionally provided in a similar olefin synthesis plant via combustion of a fuel, a carbon-based fuel, and/or a fossil fuel and/or the use of steam (e.g., that was itself generated via the combustion of such a fuel) as an intermediate heat (and/or energy) transfer fluid, is provided without combusting a fuel, a carbon-based fuel, and/or a fossil fuel and/or without the use of steam generated by the combustion of such a fuel as an intermediate heat (and/or energy) transfer fluid. In embodiments, the net energy for the overall plant or one or more sections, units or groups of like units of the plant is provided by electricity from a renewable energy source. For example, in embodiments, heating is electrically provided via resistive heating or otherwise converting electrical energy into thermal and/or mechanical energy.

In embodiments, an olefin synthesis plant of this disclosure is configured such that a majority (e.g., greater than 50, 60, 70, 80, or 90%) of the net energy needed for powering, heating, cooling, compressing, or a combination thereof utilized via one or more pyrolysis reactors, the feed preparation system, the product purification system, or a combination thereof is provided by electricity.

In embodiments, an olefin synthesis plant according to embodiments of this disclosure is a large plant having a production capacity for ethylene of greater than or equal to about 10,000 tons per year, 500,000 tons per year, 1,000,000 tons per year, 3,000,000 tons per year, or 10,000,000 tons per year. At the larger sizes anticipated in this disclosure, the amount of energy provided by a non-carbon based energy source, a renewable energy source and/or electricity will be correspondingly large. In embodiments, a partially or completely electrified plant according to the methods of this disclosure will consume greater than or equal to 50, 100, 150, 200, 250, 500, or 750 MW of electricity.

The steam cracking of hydrocarbons to produce olefins, which are major building blocks for petrochemicals, is an energy intensive process. The olefins produced via steam cracking include light olefins such as ethylene, propylene, butenes, butadiene, etc. Such olefins can be utilized, for example, in the manufacture of polymers, chemical intermediates, and synthetic rubber. Byproducts such as n-butene, isobutylene, butadiene, isoprene, and pyrolysis gasoline are also produced. The feed stream can comprise naphtha, ethane, propane, butane, LPG, condensate, gas oil, unconverted hydrowax (hydrocracker bottoms), Fischer-Tropsch wax, hydrotreated crude oil and crude oil derivatives, recycled plastics, bio-oils, or combinations thereof.

Although a specific embodiment of an olefin synthesis plant will be utilized to describe the electrification of an olefin synthesis plant, as disclosed herein, it is to be understood that numerous arrangements of units and a variety of steam cracking or other olefin synthesis technologies can be electrified as per this disclosure, as will be obvious to those of skill in the art upon reading the description herein. Furthermore, although described with reference to a specific olefin synthesis plant and method (e.g., a steam cracking plant and method), it is to be understood that electrification as described herein can be utilized in olefin synthesis plants utilizing technologies other than steam cracking (e.g., coal or petcoke gasification), and such embodiments are intended to be within the scope of this disclosure.

Figure 3:
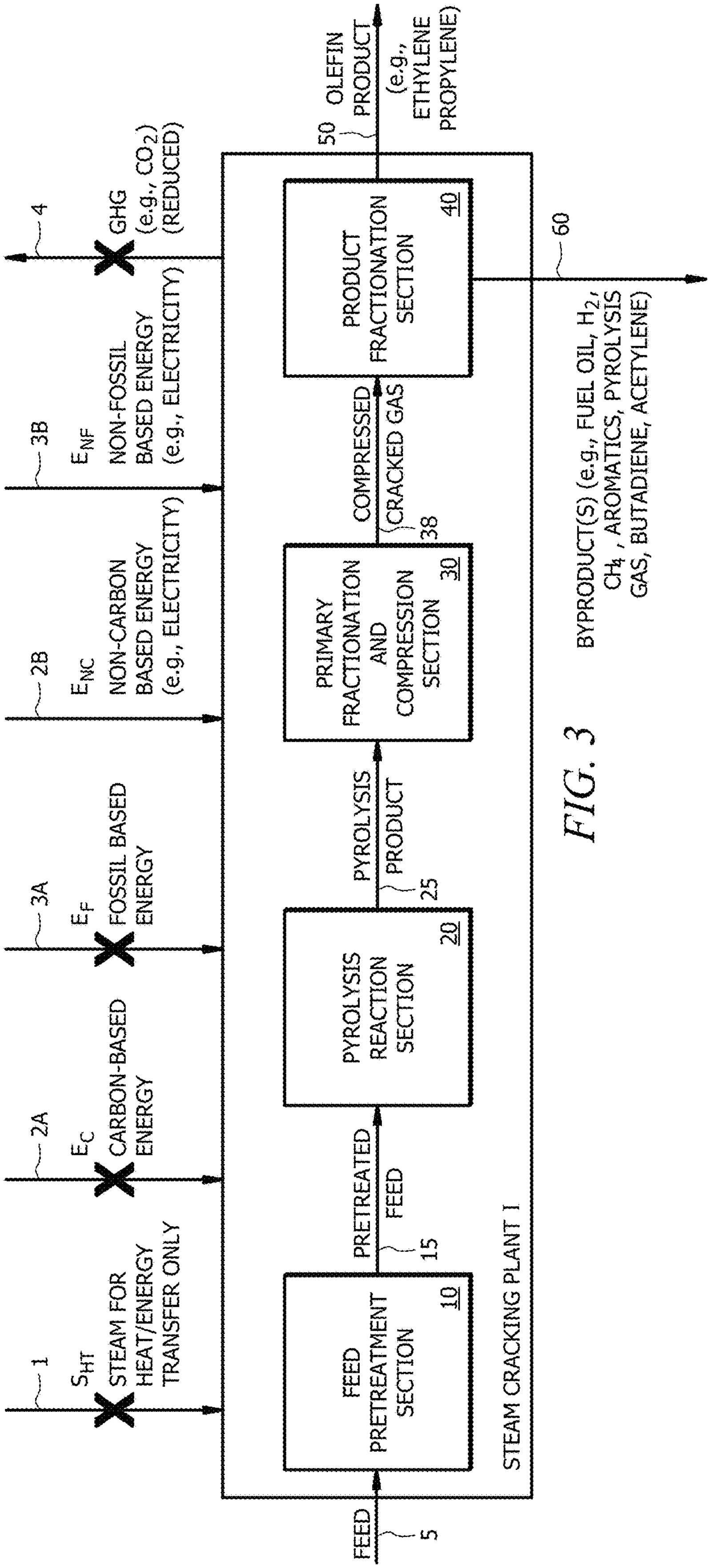
FIG. 3 shows a block flow diagram of a generalized steam cracking plant or process I, according to embodiments of this disclosure.

With reference to FIG. 3, which is a block flow diagram of a generalized steam cracking plant or process I, a steam cracking plant may be considered to include one or more of the following process sections for converting a feed stream 5 into a desired olefin product stream 50: a feed pretreatment section 10, a pyrolysis reaction section 20, a primary fractionation and compression section 30, a product fractionation or 'separation' and compression section 40, or a combination thereof. Such sections will be described briefly in the next few paragraphs, and in more detail hereinbelow.

As indicated in the steam cracking block flow diagram of FIG. 3, a feed pretreatment section 10 of a steam cracking plant I can be configured to adjust the pressure of a feed 5, possibly remove undesirable components (e.g., carbon dioxide ($CO_2$), mercury, water) from a feed, combine an incoming feed with a stored feed to minimize variations in the feed to the pyrolysis reaction section 20, and/or preheat the feed 5, to provide a pretreated feed stream 15.

The pyrolysis reaction section 20 can comprise at least one steam cracker or 'pyrolysis' furnace configured to crack hydrocarbons in the presence of steam to produce a cracked gas stream and a transfer line exchanger (TLE) or some other heat transfer device to recover heat from the cracked gas stream to provide a cooled cracked stream 25. Conventionally, the furnaces of a steam cracking plant create a high temperature environment by the combustion of fuels such as methane and hydrogen. This process is a main source of carbon dioxide emissions from a conventional steam cracking plant/process. The furnaces typically comprise a radiant section, in which the reactor tubes are heated to a temperature at which the cracking reactions occur, and a convection section, in which a feedstock is pre-heated and mixed with diluent steam prior to introduction into the reactor tube. The convection section of the furnace is also typically utilized to recover heat and generate steam, which is conventionally utilized to drive downstream compressors and for heating purposes. By one or more of the modifications of the pyrolysis section described hereinbelow, carbon dioxide emissions can be reduced, hydrocarbons (e.g., methane, ethane) conventionally burned as fuel can be utilized as additional feedstock for chemicals production, excess steam production (e.g., in addition to that utilized as a diluent in the furnace(s) of pyrolysis reaction section 20) can be reduced or eliminated and/or the energy efficiency of the furnaces can be increased.

The primary fractionation and compression section 30 can be configured to provide further heat recovery from and quenching of the cooled cracked gas stream 25, remove one or more components (e.g., fuel oil, hydrogen sulfide, carbon dioxide, water, or a combination thereof) from the cracked gas stream 25, and/or compress the cracked gas stream 25, thus providing a compressed cracked gas stream 38.

The product fractionation or separation section 40 can be configured to fractionate the compressed cracked gas stream 38, selectively hydrogenate one or more streams produced during the fractionation, and provide one or more olefin (e.g., ethylene, propylene) product streams 50. The product fractionation or separation section 40 may also provide one or more byproduct streams 60, such as, without limitation, a $C_1$ stream, a $C_2$ saturate stream, a $C_3$ saturate stream, a $C_4$ saturate stream, an acetylene stream, a butadiene stream, a 1-butene stream, an isobutylene stream, an aromatics stream, a hydrogen stream, a pyrolysis gasoline stream, and/or a fuel oil stream, or streams comprising a combination of these components. Some of these streams may be recycled to one or more sections of the steam cracking plant I. For example, without limitation, the $C_2$, $C_3$, and/or $C_4$ saturates streams may be recycled to one or more of the pyrolysis furnaces of the pyrolysis reaction section 20, hydrogen may be purified (e.g., via a pressure swing adsorption unit (PSA) and a methanation reactor to remove CO) and recycled to a hydrogenation reactor (e.g., a $C_2$, $C_3$, acetylene, or di-olefin hydrogenator) and/or utilized as a fuel source (e.g., via fuel cell). The $C_1$ stream may also be recycled for use as a fuel (e.g., for the production of hydrogen therefrom).

As depicted in FIG. 3 and mentioned above, energy (E) input to or within the steam cracking plant or one or more sections or groups of units, like units, or unit operations thereof (that may conventionally be provided via a carbon based energy ($E_C$) 2A from a carbon based energy source, a fossil fuel derived energy ($E_F$) 3A from a fossil fuel-based energy source, or via the use of steam (e.g., steam generated for this purpose using energy derived from a carbon or fossil fuel based energy source) solely or primarily as a heat or energy transfer medium ($S_{HT}$) 1), may be partially or completely replaced by non-carbon based energy ($E_{NC}$) 2B from a non-carbon based energy source, renewable/non-fossil fuel based energy ($E_{NF}$) 3B from a renewable energy source, and/or electricity (e.g., electricity and/or renewable electricity). The carbon based energy ($E_C$) 2A, the fossil fuel derived energy ($E_F$) 3A, or both can be partially or completely replaced by electricity. The electricity may be derived from a non-carbon based fuel, a renewable fuel, or a combination thereof, in embodiments. A benefit derived via the herein disclosed system and method may be a reduction in the greenhouse gas (GHG) emissions 4 from the steam cracking plant or process. The above-noted elimination or reduction of the steam system may also result in lower capital and operating costs, in embodiments.

According to this disclosure, when cooling process streams, as much heat as possible should be used to heat other process streams. However, below a certain temperature, further heat transfer is no longer effective or useful, and blowers, cooling water, and/or refrigeration (which require an energy input for heat removal) are utilized. In such embodiments, for example, heat exchangers, refrigeration units, or a combination thereof for altering the temperature of process streams may be powered electrically. In embodiments, steam is not utilized solely as an intermediate heat and/or energy transfer stream, and the plant or section(s) thereof do not comprise an elaborate steam system such as conventionally employed for energy transfer. In embodiments, steam is used as a heat transfer fluid and is not used to do mechanical work, for example to drive a pump or compressor. In embodiments, heating is provided via resistive heating. In embodiments, heating is provided via inductive heating.

Figure 4:
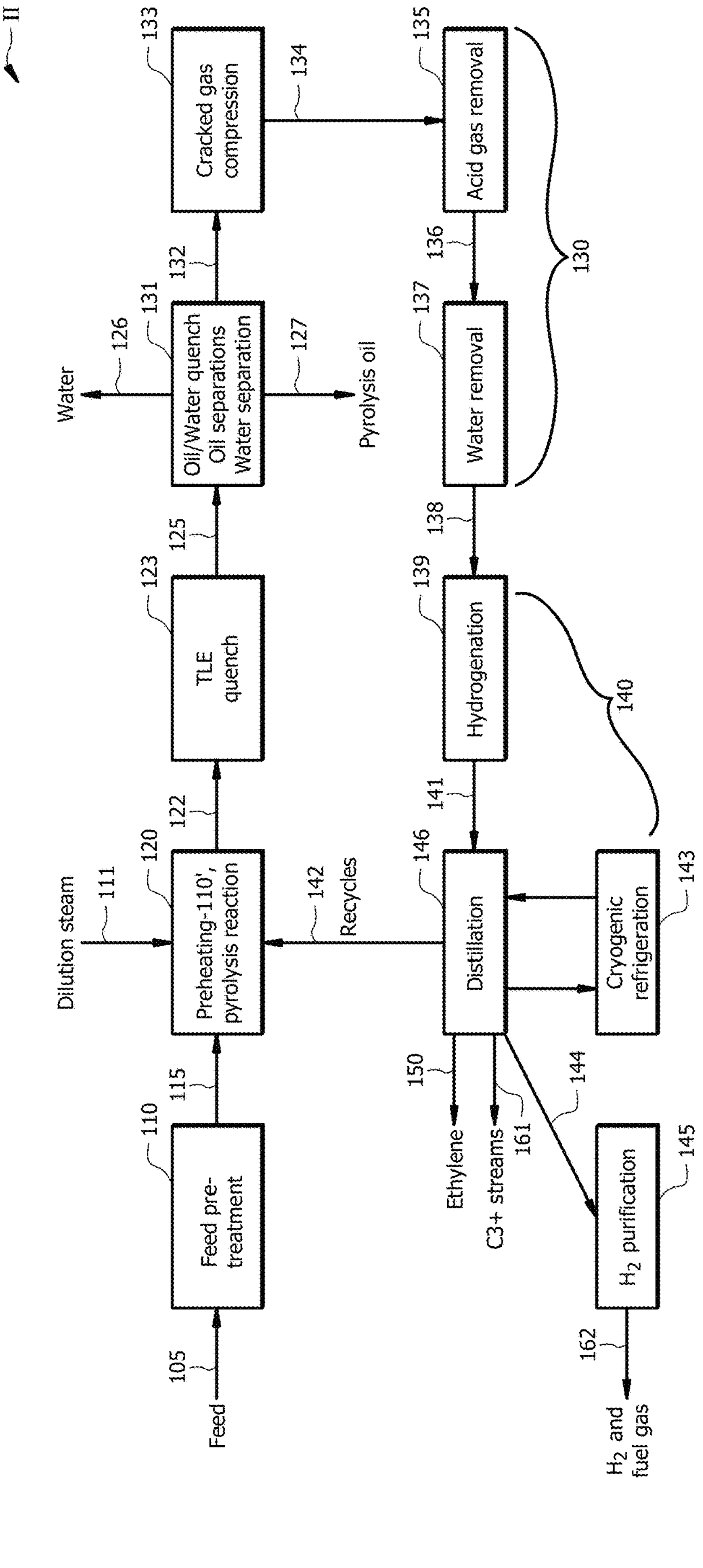
FIG. 4 shows a block flow diagram of an exemplary steam cracking plant or process II, according to embodiments of this disclosure.

Although not intending to be limited by the examples provided herein, a description of some of the ways a steam cracking plant can be electrified according to embodiments of this disclosure will now be provided with reference to the exemplary steam cracking plant II of FIG. 4. The steps, sections, units or unit operations described may be performed in any suitable order, one or more of the steps, sections, units or unit operations may be absent, duplicated, replaced by a different step, section, unit or unit operation, and additional steps, sections, units or unit operations not described herein may be employed, in various embodiments.

As noted hereinabove with reference to the embodiment of FIG. 3, in embodiments, a steam cracking plant of this disclosure comprises a feed pretreatment section 10/110. Feed is introduced to steam cracking plant II via feed stream 105. The feed is pretreated in feed pretreatment apparatus 110 to produce a pretreated feed 115. Feed pretreatment can comprise adjusting the pressure of the feed. For example, an expander may be utilized to convert feed line pressure (e.g., 500 psig) to unit pressure (e.g., about 50 psig). In embodiments of this disclosure, the energy produced during this expansion can be captured as electricity, e.g., by driving a generator. In embodiments wherein the feed 105 comprises an undesirably high level of carbon dioxide ($CO_2$), an electrically driven unit may be utilized to remove $CO_2$. For example, in embodiments, an amine absorption process can be employed, and electric heat may be utilized to strip absorbed $CO_2$ from the rich amine during regeneration. This may be utilized in place of, for example, steam stripping, potentially reducing the amount of steam needed by the $CO_2$ removal unit, the pretreatment section 10/110 of the steam cracking plant, and the overall steam cracking plant.

In embodiments wherein the feed comprises undesirable levels of mercury, feed pretreatment can further comprise mercury removal. For example, in embodiments, a mercury trap is utilized to remove mercury from feed stream 105. In such embodiments, regeneration of the mercury trap can be effected electrically (e.g., with hot gas obtained by electric heating).

In embodiments wherein substantial variation in feed composition is a concern, some feed may be stored as a liquid to minimize effects of pipeline variation in the feed. In embodiments where the feed is ethane and/or propane, refrigeration can be performed by an electric compressor and/or thermoelectric device(s). In such embodiments, the stored, cold ethane and/or propane may be used as a refrigerant before it is used as a feed, e.g., can be utilized to cool another process stream prior to introduction of the relatively warmer ethane and/or propane into pyrolysis reaction section 20/120.

Feed pretreatment 10/110 may further comprise feed preheating 110' (FIG. 4). In embodiments, feed preheating is effected to the extent possible via heat transfer with (and cooling of) the pyrolysis product gases. As feed preheating 110' can be effected by heat exchange with the products of and/or within the pyrolysis reactor(s), it is indicated, in FIG. 4, with the pyrolysis reaction section 120. The heat transfer can be effected directly by one or more feed/effluent heat exchangers and/or indirectly by using a heat transfer agent (e.g., Dowtherm or steam). As steam ('dilution steam 111'') is introduced into the hydrocarbon feed as a diluent, it may be desirable to produce steam via heat transfer with the pyrolysis product or by electric heating, and use the steam to preheat the feed by combining the relatively hotter steam with the relatively cooler feed, as such steam is not being produced solely for use as an intermediate heat or energy transfer medium in this case, but is being utilized as a diluent in the pyrolysis reactors. In embodiments, a heat exchanger utilized to preheat the feed comprises built-in heating elements. In embodiments, the feed may be preheated to a temperature higher than typically used in conventional steam cracking (e.g., for ethane to a temperature higher than 600 to 675° C.) so that more of the heat available from cooling the products of the pyrolysis reactor(s) may be utilized. In embodiments, the feed is heated to a predetermined temperature by resistive heating (e.g., via electricity flowing through a wire in thermal but not necessarily electrical contact with a pipe carrying the feed). In embodiments, heat in a radiant section of a pyrolysis reactor is utilized to preheat the feed, and the heat therein is generated electrically via any suitable methods that convert electricity into thermal energy available to preheat the feed. In embodiments, the feed is preheated by superheating dilution steam 111 before injection, and the dilution steam is heated by any of various methods of electric heating, such as mentioned hereinabove and the like. In embodiments, the steam is electrically heated to above the temperature of a cooler feed stream at the mixing point to quickly increase the temperature of the combined stream. In embodiments, the steam is electrically heated to above the temperature of the pyrolysis reactor(s) and injected into the cooler feed immediately before it enters the pyrolysis reactor(s), so that the final heating of the feed to reaction temperature occurs quickly enough to prevent unwanted reactions. In embodiments, the hot steam is injected to initiate adiabatic cracking, partially or completely reducing the energy input in the pyrolysis reactor. In embodiments, the pressure of the steam or other diluent is raised to the required process pressure by devices powered by renewable energy. Such devices can include, without limitation, vapor compressors, pumps, or closed containers that are heated electrically or supplied by heat from a renewable energy sources. In embodiments, the feed is preheated by impedance (e.g., where electricity flows through the conduit carrying the feed). In embodiments, the feed can be heated directly by ohmic heating, or a plasma, or an electric arc, or radio frequency (RF), or infrared (IR), or UV, and/or microwaves. In embodiments, the feed can be preheated by passage over a resistively heated element. In embodiments, the feed can be preheated by induction (e.g., an oscillating magnetic field). In embodiments, the feed can be heated by mechanical means driven by electricity. In embodiments, the feed can be preheated by a heat pump. In embodiments, the feed is preheated by passing hot inert gas or another medium over the tubes, and the hot inert gas or the another medium is heated electrically (e.g., via any of the preceding methods, or the like.) In embodiments, the feed is preheated by means of radiative panels that are heated electrically (e.g., via any of the preceding methods, or the like.) In embodiments, heating to the predetermined temperature can be effected by a combination of the above.

As noted above, in embodiments, to the extent possible, fuel is not burned with the concomitant production of a flue gas, and/or the production of steam (or excess steam via a general steam system) is minimized according to embodiments of this disclosure. In embodiments, energy efficiency is increased by the elimination of the flue gas, since the loss of heat contained in the flue gas to the atmosphere is eliminated. The herein-disclosed steam cracking system and method can thus provide, in embodiments, advantages in capital cost, environmental permitting and monitoring, case of operation, and/or heating designed to minimize coke formation.

As noted hereinabove with reference to the embodiments of FIGS. 3 and 4, a steam cracking plant of this disclosure comprises a pyrolysis reaction section 20/120. The pyrolysis reaction section 20/120 can comprise one or more pyrolysis reactors or furnaces, one or more transfer line exchangers (TLE), or both. The pyrolysis reactor(s) of reaction section 20/120 can be separate from feed preheating and/or integrated therewith, as indicated via box 120 in the embodiment of FIG. 4. For example, in embodiments, the pyrolysis reactor(s) can be combined with (e.g., can comprise therein) heating elements noted above for feed preheating. In embodiments, electrically heated furnaces are employed. In embodiments, only electric heating is employed and there is no convection section, no flue gas heat recovery, and/or no flue gas. In embodiments, heat is supplied electrically to radiative panels that then transfer heat to the pyrolysis reactor(s) by radiation. In embodiments, the pyrolysis furnace(s) is (are) hybrid furnaces operable via both electrical heating and fuel gas combustion. In embodiments where energy is supplied to other parts of the steam cracking with electricity but the pyrolysis section is heated by combustion, the design and/or operation of the furnace is altered (e.g., by changing the physical design, the air/fuel ratio, the fuel feed rate, and/or other variables) so that the temperature at which the hot combustion gases exit the radiation section is decreased and the amount of energy that must be recovered in the convection section is minimized. In embodiments, heat can be applied via electrical heating in the pyrolysis reaction section to enhance or optimize the resulting temperature profile relative to a pyrolysis reactor heated via combustion of a fuel (and concomitant production of a flue gas). In embodiments, electrical heating of the pyrolysis reaction section allows independent operation of heaters that would traditionally be coupled to each other via the shared flue gas flow in the convection banks. In embodiments, more precise control of heat in the pyrolysis section allows for the use of higher average pyrolysis reactor temperatures. In embodiments, electricity is utilized to generate (either directly or indirectly) free radicals to initiate the pyrolysis reaction. Such free radicals can be generated, for example, indirectly, by heating the feed hydrocarbons to a temperature such that a portion of them decompose to generate radicals, or directly, by one or more plasma sources, such as dielectric barrier discharge, cold plasma, corona discharge, glow discharge, gliding arc, spark discharge, and/or microwave plasma. The one or more plasma sources can be disposed within the pyrolysis reactor and generate plasma that controls the reactants present within the pyrolysis reactor. The free radicals can be generated, in embodiments, in situ or ex situ (e.g. within the reactor or external thereto). The free radicals can be generated, in embodiments, by a supersonic hot gas stream. The free radicals can be generated, in embodiments, by photo-dissociation under irradiation with ultraviolet (UV) or visible radiation, such as by irradiation with ultraviolet photons, vacuum-ultraviolet (VUV) photons, etc., in situ or ex situ. In embodiments, in situ radical generation occurs immediately before the feed reaches pyrolysis temperature. In embodiments, ex situ generation occurs in the presence of a carrier gas. In embodiments, this carrier gas comprises ethane, propane, or nitrogen. In embodiments, the ex situ generated radicals are injected into the feed stream immediately before the feed reaches pyrolysis temperature. In embodiments, the radicals are injected at multiple points along the length of one or more pyrolysis reactors.

In embodiments, dilution steam 111 is replaced or provided at least in part by an alternative diluent. (Reference to ‘steam cracking’ herein is intended to encompass such embodiments.) For example, in embodiments, the diluent comprises nitrogen, methane, hydrogen, or tail gas (e.g., demethanizer tail gas comprising primarily methane ($C_1$) and hydrogen ($H_2$) from a demethanizer of product fractionation section 40/140). In embodiments, the use of electricity for heating the pyrolysis reactor(s) of pyrolysis reaction section 20/120 enables the utilization of different materials for construction of the process tubes (e.g., tubes through which the feed and pyrolysis product passes) within the pyrolysis reactors.

Decoking may be reduced via the herein disclosed steam cracking plant and method of steam cracking. However, decoking may be effected via the introduction of hot air, steam, or other gases into the pyrolysis reactor tubes, in embodiments. In embodiments, the decoking gases are heated electrically, and/or electric heating is utilized to control the decoking process. In embodiments, the herein-disclosed steam cracking plant cokes more slowly than a conventional steam cracking plant (e.g., that utilizes combustion of a fuel to heat the pyrolysis reactor(s)), decokes faster, or both. In embodiments, the steam used for decoking is produced by an electric heater or an electrode boiler.

The herein-disclosed steam cracking plant can comprise a TLE 123 operable to provide a first step, rapid cooling (or 'primary quench) to stop the reaction (e.g., to rapidly reduce the temperature of the cracked gas product in cracked gas product stream 122 to about 350 to 600° C.) and produce a TLE quenched cracked gas stream 125. In embodiments, the initial TLE quench lowers the temperature only to the maximum temperature required to stop unwanted reactions from occurring and the remaining heat is removed in subsequent heat exchangers. TLE quench may be effected via gas-gas heat exchange to return heat to and thus preheat the feed. In embodiments, TLE 123 may move heat indirectly using a heat transfer medium (e.g., Dowtherm or steam). In embodiments, a TLE may comprise more than one section, whereby heat transfer can be effected at more than one temperature, thus enabling the capture of more heat than a single section TLE. In embodiments, rather than via a TLE, the pyrolysis reaction is quenched via injection of a cold fluid. According to embodiments of this disclosure, such a cold fluid may be cooled/produced electrically. In embodiments, dilution steam 111 may be generated by heat-exchange with the TLE at TLE quench 123.

As noted hereinabove with reference to the embodiments of FIGS. 3 and 4, a steam cracking plant of this disclosure comprises a primary fractionation and compression section 30/130. The primary fractionation and compression section 30/130 can be configured to provide further heat recovery from and quenching of the cooled cracked gas stream 25/125, remove one or more components (e.g., fuel oil, pyrolysis gasoline, pyrolysis oil, hydrogen sulfide, carbon dioxide, water, or a combination thereof) from the cracked gas stream 25/125, and/or compress the cracked gas stream 25/125, thus providing a compressed cracked gas stream 38/138. In embodiments, the primary fractionation and compression section 30/130 can comprise a cracked gas cooler, oil and/or water quench and/or oil and/or water separations 131 (also referred to herein as a 'quench and process water system' 131, for brevity), cracked gas compression 133, acid gas removal 135, water removal 137, or a combination thereof.

The herein-disclosed steam cracking plant can comprise a cracked gas cooler operable to extract additional heat from the TLE quenched cracked gas stream 125. Such a cracked gas cooler can operate via direct gas-gas heat exchange to preheat the feed stream 105, can be utilized to generate dilution steam, can be utilized to recover heat to be used for heat integration elsewhere in the plant (e.g., other than or in addition to preheating the feed stream 105), and/or can be utilized to generate electricity while cooling the gas (e.g., via a thermoelectric device).

In embodiments, the herein-disclosed steam cracking plant can comprise a quench (e.g., a secondary quench) and process water system, such as quench and water process system 131 of the embodiment of FIG. 4, operable to condense water and higher molecular weight hydrocarbons generated, or such a water quench system can be replaced as described below. The heat removed in quench and water process system 131 can be utilized for heat integration. In embodiments, the heat can be utilized to preheat the feed stream 105. In embodiments, a thermoelectric device may be utilized to cool the process stream directly or to cool a water quench stream 126, in some embodiments also to generate electricity. In embodiments, an absorption chiller is utilized to cool the process stream or the quench water stream 126 to a lower temperature than conventional using electric refrigeration. In embodiments, a heat pump is utilized. In embodiments, electricity is utilized to effect oil separation from quench water.

In embodiments, the herein-disclosed steam cracking plant can comprise a stripper reboiler for the process water. In such embodiments, an electric heater can be utilized to heat the process water stripper reboiler. In embodiments, an electrode boiler (e.g., operated via ohmic resistance heating by applying an electric current through the water) is utilized for vaporizing recycled process water (e.g., for generation of dilution steam 111). In embodiments, an immersion heater is used to vaporize process water. As noted above in the feed preheating section 110', in embodiments, an electric heater is utilized for dilution steam superheating, such that the steam can be superheated to a higher temperature than traditional designs. In embodiments, an electric heater is utilized on select quench water cooling applications for temperature control and to overcome temperature driving force limitations. In embodiments, a thermoelectric device may be employed to modify the quench water temperatures to further cool the water refluxing to the quench water column while heating the water for heating applications in the quench water heat recovery for better temperature driving force on both applications.

Similar electrification can be utilized for oil quench and/or oil separations of a cracked gas cooler, oil and/or water quench and/or oil and/or water separations 131 of a naphtha or gas oil cracker.

In embodiments, the herein-disclosed steam cracking plant can comprise a cracked gas compression section (or 'primary compression section') 133 comprising one or more stages (e.g., 1, 2, 3, 4, or 5 primary compression stages) for compressing the quenched cracked gas in stream 132 to produce a compressed cracked gas stream 134, each compression stage comprising one or a plurality of compressors. In embodiments, a steam turbine of conventional steam cracking plants (within the primary compression section or elsewhere in the steam cracking plant (e.g., a secondary compression section comprising one or two compression stages, each compression stage comprising one or a plurality of compressors), a propylene refrigeration compressor or compression section and/or an ethylene refrigeration compressor or compression section) is replaced with an electric motor. An electric motor (e.g., an electric-drive compressor) can be utilized for each stage of a multi-stage compression section, or certain motors may be utilized on group-specific compression stages. This may allow for optimization. In embodiments, one or more of the motors employed are variable speed motors. In embodiments, via utilization of one or more electric-drive compressors, the pressure in the downstream product separation section 40/140 can be increased, thus enabling a reduced need for refrigeration. In such embodiments, the process may entail additional compressor duty but less utility duty. In alternative embodiments, the pressure may be decreased, resulting in the need for increased refrigeration. In such embodiments, the process may entail less compressor duty but more utility duty. Such increased and decreased pressure embodiments enable unconventional optimization of pressure. Electrification of the cracked gas compressor(s) as described hereinabove may allow the elimination of a hydrocarbon-fired stand-by boiler conventionally incorporated in steam cracking plants to handle variations in the steam supply. Accordingly, in embodiments, a steam cracking plant of this disclosure does not comprise a hydrocarbon-fired boiler. In embodiments, to enhance reliability, a thermoelectric device integrated into the vapor/liquid separators upstream of one or each compression stage of cracked gas compression 133 is employed. Such a thermoelectric device will initially cool the gas and provide more condensation, but will also reheat the gas to help eliminate any liquid droplets that may be entrained, thus protecting the compressor blades from erosion by liquid droplet collision. In embodiments, one or more compressors is powered by a multi-drive system comprising an electric motor drive, a steam turbine drive, and/or a gas turbine drive. In embodiments, an electrode boiler is used to generate steam for the compressor turbine. In some embodiments, steam for the compressor turbine is produced on a continuous basis. In other embodiments, steam from the electrode boiler is only needed for a short period of time to handle intermittent operating situations.

In a conventional steam cracking plant, due to the energy intensive nature of ethylene production, most of the energy recovered from the cracked gas is used to make high pressure (e.g., 1800 psi) steam. This steam is utilized to drive turbines for compressing cracked gas, a propylene refrigeration compressor, an ethylene refrigeration compressor, pumps, and the like. According to embodiments of this disclosure steam is not utilized to provide mechanical work, e.g., to drive turbines for compressing cracked gas (e.g., in primary and/or secondary cracked gas compression sections, stages, or compressors), a propylene refrigeration compressor, an ethylene refrigeration compressor, or a combination thereof.

The herein-disclosed steam cracking plant can comprise an acid-gas removal system 135 for removing acid gas (e.g., hydrogen sulfide, carbon dioxide) from the compressed gas stream 134 to produce an acid gas-reduced stream 136. (This may be the same or a different system from the amine absorption system described in the feed pretreatment section 10/110.) Conventional acid gas removal systems are caustic scrubbers. In embodiments, such systems are replaced with an electrified amine system, whereby a spent caustic stream is not produced. The amine system can be electrified according to embodiments of this disclosure by heating a stripper employed to regenerate the amine stream with an electric heater. In embodiments, this electric heater is an immersion heater.

In embodiments, the herein-disclosed steam cracking plant can comprise a water removal apparatus or dryer configured to remove moisture, such as water removal apparatus 137 configured to remove water from acid gas-reduced stream 136 and produce a dried cracked gas stream 138. In embodiments, regeneration for the dryer is effected with an electrically heated gas. In embodiments, a vessel is electrically heated to speed up the regeneration process. In embodiments, a closed-loop system is utilized to condense water from a regeneration gas.

As noted hereinabove with reference to the embodiments of FIGS. 3 and 4, a steam cracking plant of this disclosure comprises a product fractionation section 40/140. The product fractionation or separation section 40/140 can be configured to fractionate the compressed cracked gas stream, selectively hydrogenate one or more components present in one or more streams produced during the fractionation, and provide one or more olefin (e.g., ethylene, propylene) product streams 50/150. In embodiments, the product fractionation or separation section 40/140 can comprise distillation (e.g., cryogenic distillation) 146, cryogenic refrigeration 143, di-olefin and/or alkyne hydrogenation 139, hydrogen purification, extraction, component (e.g., ethane) recycle 142, or a combination thereof.

The herein-disclosed steam cracking plant can comprise one or more refrigeration compressors of one or more refrigeration or cryogenic refrigeration sections 143 (e.g., for ethylene refrigeration, propylene refrigeration, cryogenic distillation). One or more of the refrigeration compressors can be electrified according to embodiments of this disclosure. In embodiments, additional compressors and/or stages are utilized to enable tailoring of each refrigeration loop to the individual use. In embodiments, a different working fluid, such as for example nitrogen ($N_2$), carbon dioxide ($CO_2$), or a mixture of refrigerants is utilized rather than conventional ethylene and propylene. In embodiments, feed ethane or propane may be chilled and stored when electricity (e.g., from an IES) is available or inexpensive, and used as refrigerant and feed when electricity is unavailable or expensive. In embodiments, product ethylene and/or product propylene may be chilled and stored when electricity (e.g., from an IES) is available or inexpensive, and used as refrigerant when electricity is unavailable or expensive.

In embodiments, the energy lost at each of the pressure let-down steps of refrigerant (which are adiabatic and not isentropic) can be recovered (as electricity) by utilizing power-generating turbines rather than control valves. In embodiments, rather than utilizing conventional refrigeration, which involves vapor compression, direct electric cooling (e.g., via thermoelectric devices) is utilized for part or all of the refrigeration.

The herein-disclosed steam cracking plant can comprise one or more distillation or cryogenic distillation columns of a distillation section configured to perform product fractionation of the cracked gas stream, as indicated in FIG. 4 with cryogenic distillation section 146 configured to fractionate the cracked gas introduced thereto via cracked gas distillation feed stream 141. In the embodiment of FIG. 4, distillation section 146 is configured to produce an ethylene product stream 150, a $C_{3+}$ stream 161, a hydrogen- and methane-containing stream 144, and an ethane recycle stream 142, which can be returned to the pyrolysis reaction section 120.

The fractionation system can comprise one or more of a demethanizer, a deethanizer, a $C_2$ splitter, a depropanizer, a $C_3$ splitter, a debutanizer, an acetylene hydrogenator, a $C_3$ hydrogenator, or any suitable combination thereof; the order of these steps may be varied accordingly by one skilled in the art without departing from the spirit and teachings of the disclosure. The steam cracking plant can further comprise one or more recycle lines configured to return the ethane, the propane, or other hydrocarbon fractions, individually or in common, to the pyrolysis section 20/120. The steam cracking plant can further comprise a butadiene extraction apparatus downstream of the debutanizer and configured to separate butadiene; an acetylene hydrogenation apparatus upstream or downstream of the $C_2$ splitter and configured to hydrogenate acetylene; an acetylene separator; a methylacetylene and propadiene (MAPD) hydrogenator upstream of the $C_3$ splitter and configured to hydrogenate methylacetylene and/or propadiene (allene); or a combination thereof.

In embodiments, one or more distillation columns where the heat is supplied and/or removed electrically are employed in the distillation section 146. In embodiments, one or more of the distillation columns has an electrically-controlled temperature profile, which may enable more precise control of the predetermined temperature profile therein. In embodiments, one or more of the distillation columns is configured for operation with one or more electrically-driven reboilers.

In embodiments, heat pump arrangements are utilized to electrically heat and cool towers (also referred to herein as distillation columns). The heat pumps may be integrated with the refrigeration system 143. Optimization among heat pumps, refrigeration system, and/or electrically heated reboilers may be performed.

In embodiments, a vent gas from one or more of the distillation towers (e.g., a vent from a deethanizer) of the cryogenic distillation section 146 may be cooled using one or more thermoelectric coolers, in some embodiments also to produce electricity.

In embodiments, all or part of the cryogenic distillation system is replaced with a solvent system or an adsorbent system, with the energy therefor being supplied by electric heating. In embodiments, electric heaters, coolers, and/or heat pumps are utilized in conjunction with a reactive distillation system.

In embodiments, the herein-disclosed steam cracking plant produces one or more streams 144 comprising hydrogen, methane, or both, and the cracking plant can further comprise a pressure swing adsorber (PSA), gas-permeable membrane, cryogenic distillation apparatus, or other hydrogen purification apparatus 145 for recovering hydrogen. In embodiments, pressurization of the PSA can be electrified. In embodiments, refrigeration for the cryogenic distillation can be electrified. The recovered hydrogen can be utilized within the steam cracking plant, such as for $C_2$, $C_3$, di-olefin, and/or acetylene hydrogenation 139. In embodiments, hydrogen is exported for further chemical use (e.g., to an ammonia plant, methanol plant, or a refinery) rather than burned to make heat. Recovered methane can be utilized, for example, as a feed for another plant, such as, without limitation, an ammonia synthesis plant or a methanol synthesis plant. In embodiments, methane is exported to a methanol synthesis plant rather than burned to make heat. In embodiments, a gas comprising a mixture of methane and $H_2$ is not purified, and may be sent to other off-site or on-site units (e.g., for methanol or ammonia synthesis). The ammonia synthesis plant and/or the methanol synthesis plant may or may not also be electrified similarly to the manner described herein.

In embodiments, the one or more streams 144 comprising hydrogen, methane, or both, can be fed to a fuel cell to purify methane and produce electricity. In embodiments, the purified hydrogen obtained from hydrogen purification apparatus 145 can be fed to a fuel cell to produce electricity. In embodiments, compressed or adsorbed hydrogen is stored when renewable electricity (e.g., from a renewable IES) is available and utilized to make electricity via fuel cell(s) when the IES is unavailable or expensive, for example when electricity from a renewable source such as solar is available during the day, but not at night. In embodiments, gaseous or liquid ethane or propane is stored, and liquid ethane or propane is utilized as a refrigerant later (e.g., at night), for example when electricity from a renewable source such as solar is available during the day, but not at night. In embodiments, liquid ethylene or propylene is stored and utilized as a refrigerant later (e.g., at night), for example when electricity from a renewable source such as solar energy is available during the day, but not at night.

In embodiments, the herein-disclosed steam cracking plant comprises one or more hydrogenation apparatus, such as, without limitation, an acetylene hydrogenation apparatus, an methylacetylene and propadiene (MAPD) hydrogenation apparatus, and/or other hydrogenation apparatus. Such hydrogenation apparatus is indicated in FIG. 2 at box 139. In embodiments, the herein-disclosed steam cracking plant comprises an acetylene or di-olefin hydrogenation apparatus at box 139, although hydrogenation may be carried out between distillation columns of cryogenic distillation 146. Dried cracked gas introduced into such a hydrogenation apparatus (e.g., via stream 138) may, according to embodiments of this disclosure, be preheated using electricity. In embodiments, intercoolers, if any, can be operated via heat pump or electric cooling.

In embodiments, a majority, greater than 20, 30, 40, 50, 60, 70, 80, or 90%, or substantially all of the net heat input or removal needed within the steam cracking plant is provided from a non-carbon based energy source, from a renewable energy source, such as renewable electricity, from electricity (e.g., electricity from a renewable and/or non-renewable source), or a combination thereof.

In embodiments, a majority, greater than 20, 30, 40, 50, 60, 70, 80, or 90%, or substantially all of the net energy needed for compression of cracked gas (e.g., in primary cracked gas compression 133 and/or secondary cracked gas compression sections, stages, or compressors), refrigeration (e.g., a propylene refrigeration compressor, an ethylene refrigeration compressor, or a combination thereof), and/or elsewhere within the steam cracking plant is provided from a non-carbon based energy source, from a renewable energy source (e.g., an $E_{NF}$ energy source), such as renewable electricity, from electricity (e.g., electricity from a renewable and/or non-renewable source), or a combination thereof. For example, an electric motor, an electrically-driven turbine, and/or a turbine driven by steam produced electrically may be utilized to provide compression throughout the steam cracking plant or one or more sections thereof. In embodiments, a majority, greater than 20, 30, 40, 50, 60, 70, 80, or 90%, or substantially all of the compressors are replaced by or utilize an electric motor, an electrically-driven turbine, and/or a turbine driven by steam produced electrically. In embodiments, electricity can be used to provide the motive force for fluids. For example, electricity can be used to power pumps to move and/or pressurize liquids, and/or to power air blowers and/or fans. In embodiments, a fraction, a majority (e.g., 20, 30, 40, 50, 60, 70, 80, 90, or 100%), or substantially all of a number of pumps utilized in the olefin synthesis plant are electrified.

In embodiments, electricity is utilized to produce slightly colder (e.g., 2, 5, 10 or 15° C. colder) than conventional cooling water for cooling within one or more sections of the herein-disclosed olefin synthesis plant. In embodiments, nitrogen, methane, or $CO_2$ may be utilized in the cracker at pyrolysis reaction section 20/120 for primary quench.

As noted above, when utilizing electricity from a renewable source that has a potentially or known intermittent supply (e.g., an intermittent energy source or IES), various steps can be taken to maintain operation of the steam cracking plant, according to embodiments of this disclosure. Such handling of an IES can be as described in U.S. Provisional Patent Application Nos. 62/792,636 and 62/792,637, entitled Use of Intermittent Energy in the Production of Chemicals, which are being filed on Jan. 15, 2019, the disclosure of each of which is hereby incorporated herein for purposes not contrary to this disclosure. For example, in embodiments, compressed hydrogen is stored for intermittency of electric supply. Alternatively or additionally, one or more cryogenic liquids can be stored for intermittency of electric supply. Alternatively or additionally, heat can be stored for intermittency of electric supply. Alternatively or additionally, batteries can be kept for intermittency of electric supply. Backup power for key components may be provided; non-renewable electricity may be utilized as a back-up for intermittent renewable electricity. For example, such backup power may be produced via apparatus driven by compressed gas or a flywheel.

Electrification of the steam cracking plant of this disclosure can be provided via an electricity supply that can be high voltage or low voltage. The electric devices can be operable or operated on alternating (single or multiphase) or direct current.

In embodiments, steam generated by the combustion of fuels or produced solely for heat and/or energy transfer is not utilized in a steam cracking system and method of this disclosure (e.g., in the feed pretreatment section 10/110, the pyrolysis reaction section 20/120, the primary fractionation and compression section 30/130, and/or the product fractionation section 40/140). In this manner, an olefin synthesis plant according to this disclosure can be operated, in embodiments, without an elaborate steam heat and/or energy transfer system (which may be conventionally utilized in an olefin synthesis plant). In some applications, for example where steam is utilized within a reactor as a feed component and/or diluent, such steam may be produced via heat transfer with a process stream within the chemical synthesis plant and/or may be produced electrically. In embodiments, steam generated via heat transfer with a process stream may be superheated using electricity. In embodiments, steam is not utilized throughout the olefin synthesis plant as a commodity or utility. In embodiments, an olefin synthesis plant of this disclosure is essentially steam-free, or utilizes substantially less steam (e.g., uses at least 10, 20, 30, 40, 50, 60, 70, 80, 90, or 100 volume percent (vol %) less steam) than a conventional olefin synthesis plant. For example, a conventional plant for producing olefins may utilize steam production for reboilers of distillation columns of the feed pretreatment section 10/110 and/or the product purification section 40/140, may utilize steam production to drive steam turbines for compressing process and/or recycle streams, or may utilize steam production to drive steam turbines for refrigeration. In embodiments, steam is not produced, or substantially less steam is produced (e.g., the process uses at least 10, 20, 30, 40, 50, 60, 70, 80, 90, or 100 volume percent (vol %) less steam), for these operations in a chemical plant according to this disclosure. In embodiments, steam is used as a heat transfer fluid, but is not used to do mechanical work (e.g., to drive a compressor or pump.) In embodiments, the steam generated for these operations is primarily (e.g., of the total steam utilized, the greatest percentage is electrically produced), mainly (e.g., greater than 50% of the steam is electrically produced) or substantially all electrically produced. In embodiments, the steam utilized as a reactant or diluent is primarily (e.g., of the total steam utilized, the greatest percentage is electrically produced), mainly (e.g., greater than 50% of the steam is electrically produced) or substantially all electrically produced.

In embodiments, in an olefin synthesis plant or process of this disclosure, more energy is utilized directly 'as-is', for example, utilizing heat from a hot product effluent stream to heat a feed stream, rather than being transformed, e.g., via the generation of steam and the conversion of the thermal energy to mechanical energy via a steam turbine. According to embodiments of this disclosure, the use of energy directly can increase the energy efficiency of the olefin synthesis plant, for example by reducing energy efficiency losses that occur when heat is converted to mechanical energy.

As energy consumption represents a large percent of the operating cost for a traditional olefin synthesis plant, increasing energy efficiency (e.g., via electrification) as per this disclosure and/or utilizing methane or hydrogen conventionally burned to provide heat for reforming and/or burned for compression (e.g., burned to produce steam for a steam turbine or burned for a gas turbine) to produce additional product (e.g., methanol from methane and/or ammonia from hydrogen) may provide economic advantages over a conventional olefin synthesis plant. Concomitantly, the reduction of the burning of fossil fuels (e.g., natural gas, methane) as a fuel enabled via this disclosure provides for reduced greenhouse gas (GHG) emissions relative to a conventional olefin synthesis plant in which hydrocarbons are burned as fuel. In embodiments, GHG emissions (e.g., carbon dioxide emissions) are reduced by at least 5, 10, 20, 30, 40, 50, 60, 70, 80, 90, or 100% relative to a conventional olefin synthesis plant in which hydrocarbons are burned as fuel. In embodiments, $CO_2$ production is reduced to less than or equal to about 1.5, 1.2, 1.0, 0.75, 0.5, 0.2, or 0 tons $CO_2$ per ton chemical product (e.g., olefin(s), such as, without limitation, ethylene) produced. In embodiments, aspects of this disclosure can lead to an increase in carbon efficiency of a process (i.e., to an increase of the fraction of carbon consumed in the process that reappears as a useful product), and/or a reduced specific energy consumption (e.g., the energy utilized to synthesize a quantity of the chemical product 50).

Conventionally, the energy required for unit operations in chemical processes is generally provided by the burning of fossil fuels, especially natural gas. Herein-disclosed are systems and methods by which this energy input can be reduced or replaced, in embodiments, with non-carbon based energy $E_{NC}$, renewable energy $E_{NF}$, such as renewable electricity, and/or by electricity from any source (e.g., renewable and/or non-renewable), such that energy efficiency is improved (e.g., energy losses are reduced). The herein-disclosed use of non-carbon based energy $E_{NC}$, renewable energy $E_{NF}$, and/or electricity in the production of chemicals, such as the production of olefins via cracking, increases energy efficiency of and/or decreases and/or eliminates carbon dioxide emissions from and fossil fuel consumption within the olefin synthesis process. In embodiments, the energy efficiency of the process is reduced such that the specific energy consumption (the total net energy input, including fuel and electricity, to the process divided by the production rate) is less than or equal to 17, 16, 15, 14, 13, 12, 11, 10, 9, or 8 GJ/ton of ethylene produced, where if fuel is consumed, the specific energy consumption is calculated using the higher heating value of the fuel.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

In FIGS. 5-9 associated with the Examples, a lightning bolt symbol is utilized to represent electricity, specifically renewable electricity, while a triple elongated 'S' symbol is utilized to indicate steam usage. In FIGS. 5-9 and the description of the Examples below, pumps and miscellaneous energy sinks are denoted as 217.

Comparative Example 1

A process simulation was performed to determine the heat and mass flows for a typical process III for the production of ethylene by the steam cracking of ethane. The process simulation utilized in this Comparative Example 1 was made using Aspen Plus®. It does not represent a specific operating plant, but it is representative of a typical plant as described hereinbelow with reference to FIG. 5; the design parameters were taken from knowledge of specific plants, as well as literature information on typical process operations. Although variations will be obvious to one skilled in the art, this Comparative Example 1 represents a typical process that can be used as a basis for comparing the effects of electrification modifications according to embodiments of this disclosure.

The process of Comparative Example 1 is configured to produce 187.5 metric tons per hour of ethylene. If operated for a typical 8000 hours in a year, this would result in the production of 1.5 million tons of ethylene, although variations in downtime due to upsets and maintenance could increase or reduce this output. This size is typical of the largest ethane crackers being built today. At this scale, eight to twelve individual cracking furnaces would typically be used, with each furnace containing multiple reactor tubes. Because the tubes build up coke and other deposits, individual furnaces must be taken off-line periodically for regeneration; the plant may typically operate with between six and twelve furnaces at a time.

Figure 5:
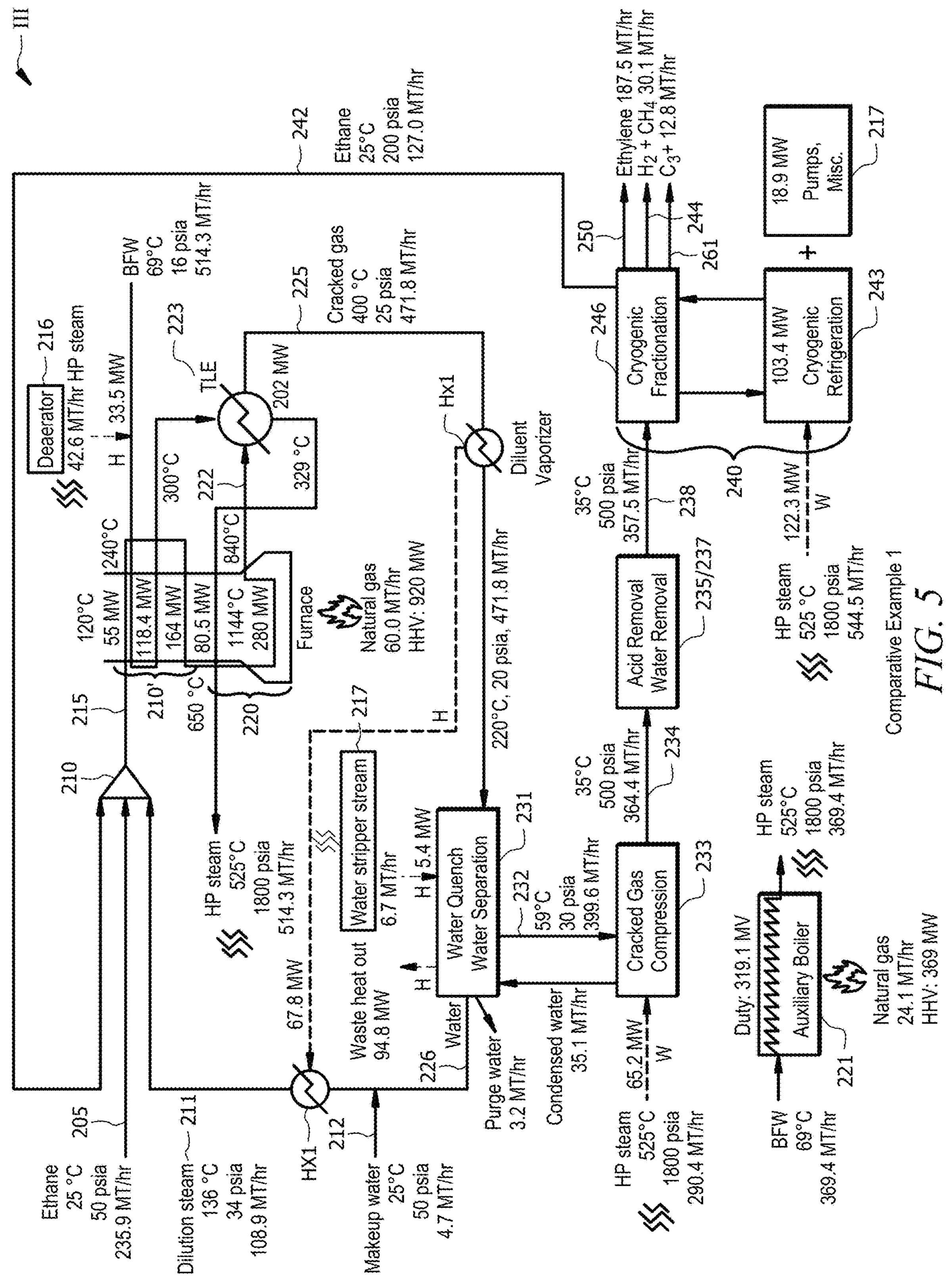
FIG. 5 shows operating parameters for a conventionally operated olefin synthesis plant III utilized in Comparative Example 1.

As shown in FIG. 5 (which has been simplified to show only the essential features of the process of this Comparative Example 1), 236 metric tons per hour (t/hr) of ethane feed 205 are fed to the process and combined in a mixer of feed pretreatment section 210 with recycle ethane in ethane recycle stream 242 and diluent steam in dilution steam stream 211; the combined feed stream 215 is heated to 650° C. in the convection sections of the furnaces of feed preheating section 210' and then heated to a reaction temperature of 840° C. in reactor tubes contained within the radiant sections of the furnaces of pyrolysis section 220. These radiant sections also supply the heat of reaction for the ethane cracking, which is endothermic. A deaerator 216 may provide deaerator steam that is injected into the boiler feed water to remove oxygen and other dissolved gases before entering the convection sections of the furnaces of feed preheating section 210', as indicated in FIG. 5. The exiting process gas in cracked gas product stream 222 is cooled to 400° C. in a transfer line exchanger (TLE) 223 and further cooled by exchange of the product in TLE quenched cracked gas stream 225 in heat exchanger HX1 which vaporizes the water in lines 212 and 226. The diluent water is then recovered by quenching in water quench 231; the recovered water in water line 226 is returned for reuse as diluent in the pyrolysis reaction section 220. Water quench 231 can involve a water quench tower and a water stripper which, in the embodiment of FIG. 5, can employ water stripper steam. The products in quenched cracked gas stream 232 are compressed in cracked gas compression 233, and the compressed cracked gas stream 234 is dried and acid gas impurities are removed in acid gas removal/water removal 235/237 to produce dried cracked gas stream 238. Dried cracked gas stream 238 is subjected product fractionation 240 via cryogenic fractionation 246 and associated cryogenic refrigeration 243, which is operated to separate the products and byproducts. Along with the recycle ethane in recycle ethane stream 242, the products and byproducts include 187.5 t/hr of ethylene in ethylene product stream 250, 30 t/hr comprising a mixture of hydrogen and methane in hydrogen- and methane-containing stream 244, and 13 t/hr of $C_{3+}$ products in $C_{3+}$ stream 261 comprising primarily propylene and butadiene.

In addition to a number of smaller users, there are five major energy consumers in the conventional process III of this Comparative Example 1 (see Table 2, discussed further hereinbelow): (1) vaporization of the recycle and makeup water (e.g., in heat exchanger HX1) to produce diluent steam. (2) heating of the feed gases to near reaction temperature in the convection sections of the furnaces (e.g., of feed preheating section 210'), (3) heating of the cracking furnaces and reactors (e.g., of pyrolysis reaction section 220) to supply the final temperature rise of the feed gases to reaction temperature and the heat of reaction in the radiant sections of the cracking furnaces, (4) energy to drive the cracked gas compressor (e.g., of cracked gas compression 233), and (5) energy to drive the cryogenic fractionation (e.g., cryogenic fractionation 246 of product fractionation section 240). Smaller amounts of energy are used for a variety of other purposes. As is common practice, very little electricity is consumed in Comparative Example 1, primarily for some smaller pumps at 217; some electricity is generated on site from gas expansion in the demethanizer by a power-generating turbine and amounts to only 1.6 MW. Some of the energy used can be obtained by heat exchange with the product stream as it is cooled, but the rest is conventionally generated by burning fuel. In Comparative Example 1, there are two locations which utilize external sources of energy. The first is in the cracking furnaces, which together consume 60 t/hr of natural gas with a contained chemical energy (high-heating value, or HHV) of 920 MW. The remaining energy is supplied by an auxiliary boiler 221 that converts 24.1 t/hr of natural gas with a contained chemical energy of 369 MW to high pressure (HP) steam. How to most efficiently allocate this energy to the various consumers of energy in the process with the highest efficiency is an engineering problem common to all chemical plants and requires careful matching of temperatures, types of energy, and energy content. Some of the energy can be transferred directly via heat exchange, while some is conventionally converted to steam that can either be used for heat exchange or to do mechanical work, such as drive a compressor. In Comparative Example 1 a typical strategy has been adopted for matching heat inputs and outputs, but other arrangements are possible, as will be obvious to one skilled in the art. The use of combustion furnaces to supply the external energy input needed for the process comes with a concomitant disadvantage—the stack or flue gas from these furnaces contains energy that cannot be usefully recovered because of its low temperature. For example, in the process of Comparative Example 1, this unrecovered energy, sometimes referred to as stack losses, amounts to 174 MW. Energy is also lost in several process steps, for example in water quench 231.

Table 2 shows an energy balance for the process of Comparative Example 1. As seen in Table 2, an amount of 1289 MW of chemical energy is supplied through the combustion of natural gas in the cracking furnaces of pyrolysis reaction section 220 and the auxiliary boiler 221; this represents the total net energy input to the process, although an additional 310 MW are transferred internally, for example in the cooling of the product gases from the cracking tubes. An amount of 759 MW, or roughly half of the total energy used, is transferred to the steam system, where it is primarily employed to drive the cracked gas compressor of cracked gas compression 233 and to supply energy for cryogenic refrigeration at 243. However, because energy in the form of steam is inefficiently converted to mechanical work, the amount of energy actually used in the cracked gas compressor of cracked gas compression 233 and in cryogenic refrigeration at 243 is significantly less than the energy applied as steam, as shown in Table 2. In addition, as noted above, 174 MW, or 13.5% of the net external energy supplied, is lost in the flue gas as stack losses from the cracking furnaces and auxiliary boiler and in various process losses, for example in the quench system 231.

Table 3 provides relevant energy use statistics for the process of Comparative Example 1. As seen in the data in Table 3, the total fuel gas consumption is 673,000 tons per year. The combustion of this fuel results in the atmospheric emissions of 231 t/hr of $CO_2$, or 1.85 million tons of $CO_2$ annually. Specific energy consumption (calculated used the high heating value of the fuel) is 24.7 GJ per ton of ethylene produced; 64% of this energy is lost in the stack gas, the water quench 231 and other process steps, and the inefficiencies of converting steam to mechanical work (e.g., for cracked gas compression at 233 and cryogenic refrigeration at 243.)

Example 1

Example 1 is a partial electrification as per an embodiment of this disclosure of the steam cracking process described in Comparative Example 1. In Example 1, the auxiliary boiler is removed and the energy that had been supplied to that boiler by the combustion of natural gas is replaced by a smaller amount of renewable electricity. This substitution of external energy requires some reconfiguration of the energy integration of the process; in Example 1, the most important differences are (1) the cryogenic refrigeration system and some pumps are now driven by electric motors, (2) some of the energy required for the vaporization of the recycle water to make diluent steam is provided by electric heating, and (3) the TLE has been replaced by a heat exchanger system such that much of the heat recovered from cooling the hot product gases is used to preheat the feed gases.

Figure 6:
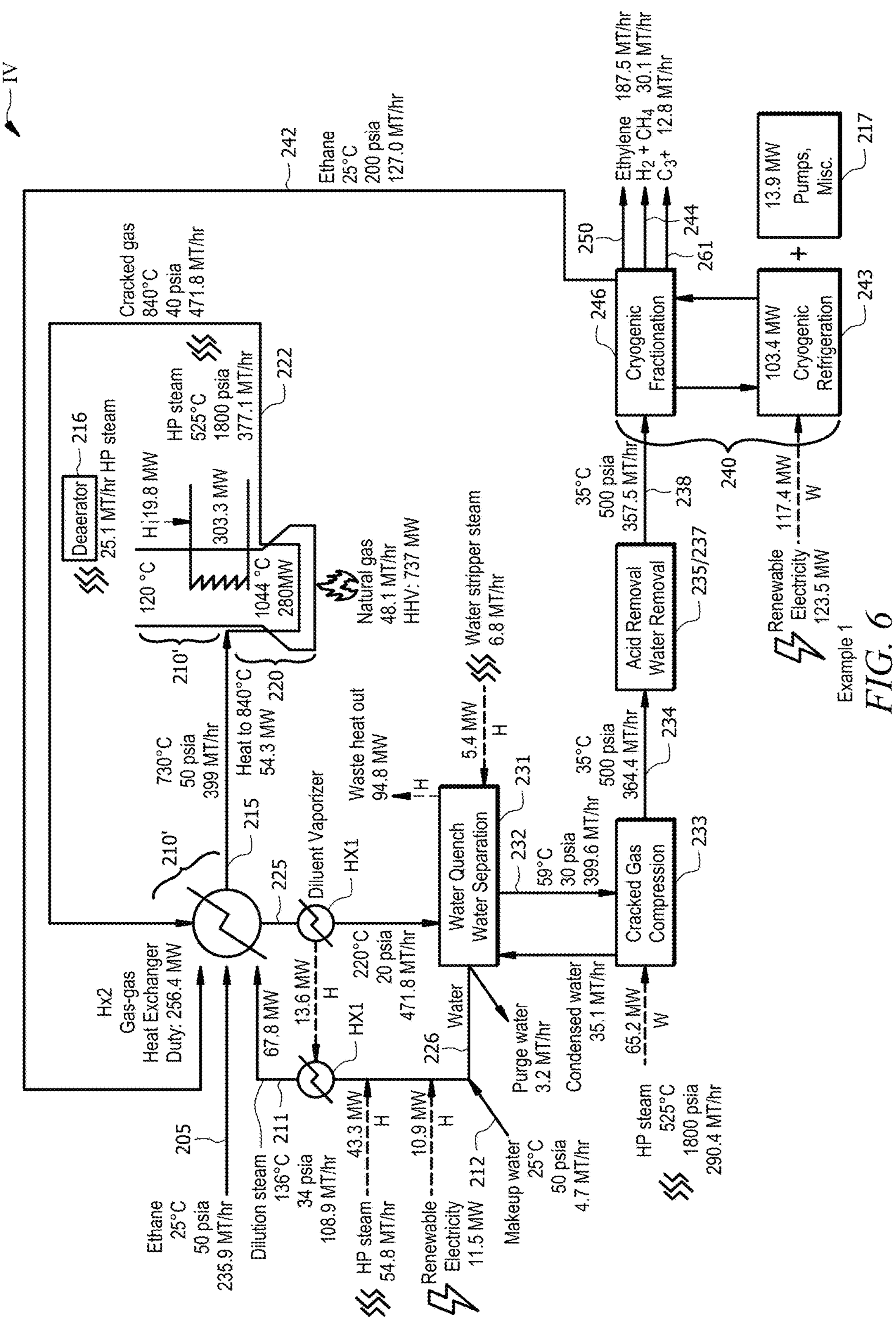
FIG. 6 shows operating parameters for an olefin synthesis plant IV electrified as per an embodiment of this disclosure and presented in Example 1.

The key elements of this electrified plant IV of Example 1 are shown in FIG. 6. As in Comparative Example 1, an amount of 236 t/hr of ethane feed 205 are combined with recycle gases in ethane recycle stream 242 and diluent steam stream in dilution steam 211; the combined feed stream 215 is heated to 730° C. by heat exchange with cooling product gases in a heat exchanger system HX2 of preheating section 210'. This heat exchange can be achieved by a variety of methods, for example one feed/effluent heat exchanger, a series of feed/effluent heat exchangers, or one or more feed/effluent heat exchangers together with one or more product heat exchangers using steam to receive the heat coupled with feed heat exchangers in which the energy of the steam is transferred to the feed stream. For the purposes of this example, one feed/effluent heat exchanger has been employed; however the specific design of the heat exchanger system HX2 can vary, as long as it is configured/utilized to extract as much of the heat as possible via cooling the product gases and utilize the thermal energy to preheat the feed gases. The feed stream is then cracked at 840° C. in the radiant furnaces of pyrolysis reaction section 220 fired by natural gas; however, since it is a goal to produce less steam than conventional, such as produced in Comparative Example 1, the exit temperature of the radiant sections of pyrolysis section 220 has been lowered by changes in furnace design and operation to decrease the heat that must be recovered in the convection sections of feed preheating section 210'. The product gases in cracked gas product stream 222 are cooled in a feed/effluent heat exchanger of heat exchanger system HX2 as described above, and further cooled by heat exchange in heat exchanger HX1 of the feed/effluent heat exchanged product in stream 225 with the recycle and makeup water in lines 212 and 226. Diluent water is then recovered by quenching in water quench 231; the recovered water in water line 226 is returned for use as diluent in the pyrolysis reaction section 220. The products in quenched cracked gas stream 232 are compressed in cracked gas compression 233, and the compressed cracked gas stream 234 is dried and acid gases are removed in acid gas removal/water removal 235/237 to produce dried cracked gas stream 238. In Example 1, in contrast to the conventional plant described in Comparative Example 1, the heat for the regeneration of the cracked gas drier absorbent material is provided electrically. Dried cracked gas stream 238 is subjected to product fractionation 240 via cryogenic fractionation 246 and associated cryogenic refrigeration 243, which is operated to separate the products and byproducts. Along with the recycle ethane in recycle ethane stream 242, the products and byproducts include 187.5 t/hr of ethylene in ethylene product stream 250, 30 t/hr comprising a mixture of hydrogen and methane in hydrogen- and methane-containing stream 244, and 13 t/hr of $C_{3+}$ products in $C_{3+}$ stream 261 comprising primarily propylene and butadiene.

In addition to a number of smaller users, there are five major energy consumers in the partially electrified process IV of Example 1 (see Table 2): (1) vaporization of the recycle and makeup water (e.g., in heat exchanger HX1) to produce diluent steam. (2) heating of the feed gases to near reaction temperature (e.g., via heat exchanger system HX2), (3) heating of the cracking reactor (e.g., of pyrolysis reaction section 220) to supply the final temperature rise to reaction temperature and the heat of reaction, (4) power to drive the cracked gas compressor (e.g., of cracked gas compression 233), and (5) energy to drive the cryogenic fractionation (e.g., cryogenic fractionation 246 of product fractionation section 240). Smaller amounts of energy are used for a variety of other purposes. Some of this energy can be obtained by heat exchange with the product stream as it is cooled, but the rest must be supplied externally. In Example 1, there are two locations which utilize external sources of energy. The first is in the cracking furnaces of pyrolysis reaction section 220, which together consume 48 t/hr of natural gas with a contained chemical energy of 737 MW. The remaining energy is supplied by 135 MW of renewable electricity. Note that, in contrast to Comparative Example 1, the plant of Example 1 does not contain an auxiliary boiler. This energy can be allocated most efficiently to the various consumers of energy in the process by careful matching of temperatures, types of energy, and energy content. Some of the energy can be transferred directly via heat exchange, while some heat is converted to steam that can either be used for heat exchange or to do mechanical work, such as drive a compressor; electricity can be used either for heating or for mechanical work. In Example 1 a logical strategy has been adopted for matching heat inputs and outputs, but other arrangements are possible, and intended to be within the scope of this disclosure. In this Example 1, 109 MW of renewable electricity are used to supply energy to the cryogenic fractionation system 240. Because this energy can be applied with high efficiency (assumed here to be 95%), this electrical energy can replace 398 MW of energy supplied as steam in Comparative Example 1. An additional 14 MW of electricity is used to power several water pumps at 217 that were driven by steam in Comparative Example 1, again with much higher efficiency. Renewable electricity is also used to supply 11.5 MW of some of the needed heat for recycle and diluent water vaporization. As in Comparative Example 1, some energy is lost in the water quench 231 as well as in other process steps. However, Example 1 according to this disclosure produces a significantly smaller amount of flue gas from combustion, such that the amount of energy that is lost in this flue gas (i.e., the stack losses) is proportionately smaller, here only 99 MW.

Table 2 shows an energy balance for the partial electrification process of Example 1. An amount of 737 MW of chemical energy are supplied through the combustion of natural gas and 135 MW of renewable electricity are supplied; this represents a total net energy input to the process of 872 MW, or 32% less than in Comparative Example 1. Additionally, 297 MW are transferred internally according to this disclosure according to Example 1, for example during the cooling of the product gases. An amount of 323 MW is transferred to the steam system in Example 1, which is less than half of the amount that is required in Comparative Example 1. In Example 1, the majority of this energy is used to drive the cracked gas compressor of cracked gas compression 233. Total losses from the system from the flue gas, inefficiencies in the use of steam and electricity, and losses in the quench system and other process steps are 50% less than in Comparative Example 1.

Table 3 provides relevant energy use statistics for Example 1 according to this disclosure. In Example 1, the total natural gas consumption is 385,000 tons per year. The combustion of this fuel results in the atmospheric emissions of 132 t/hr of $CO_2$, or 1.06 million tons of $CO_2$ annually; this represents a 45% decrease over Comparative Example 1. The 288,000 tons per year of natural gas saved can be used elsewhere, for example as a feed for a methanol or ammonia synthesis process. Specific energy consumption is 16.7 GJ per ton of ethylene produced, which is 32% less than in the process of Comparative Example 1. A reduced amount of 47% of the net external energy supplied is lost in the stack gas, the water quench 231 and other process steps, and the inefficiencies of converting steam or electricity to shaft work (e.g., for cracked gas compression at 233 and cryogenic refrigeration at 243), a significant improvement over Comparative Example 1.

Example 2

Example 2 is a complete electrification as per an embodiment of this disclosure of the steam cracking process described in Comparative Example 1. In Example 2, the energy supplied by the natural gas-fired auxiliary boiler and cracking furnaces in Comparative Example 1 is replaced with renewable electricity, which powers all compressors and pumps, supplies the energy for cracking, and provides heat for the vaporization of the recycle and makeup water. Also, the TLE of Comparative Example 1 has been replaced by a heat exchanger system such that much of the heat recovered from cooling the hot product gases is used to preheat the feed gases. These changes allow for the elimination of the process steam system and complete avoidance of flue gas losses.

Figure 7:
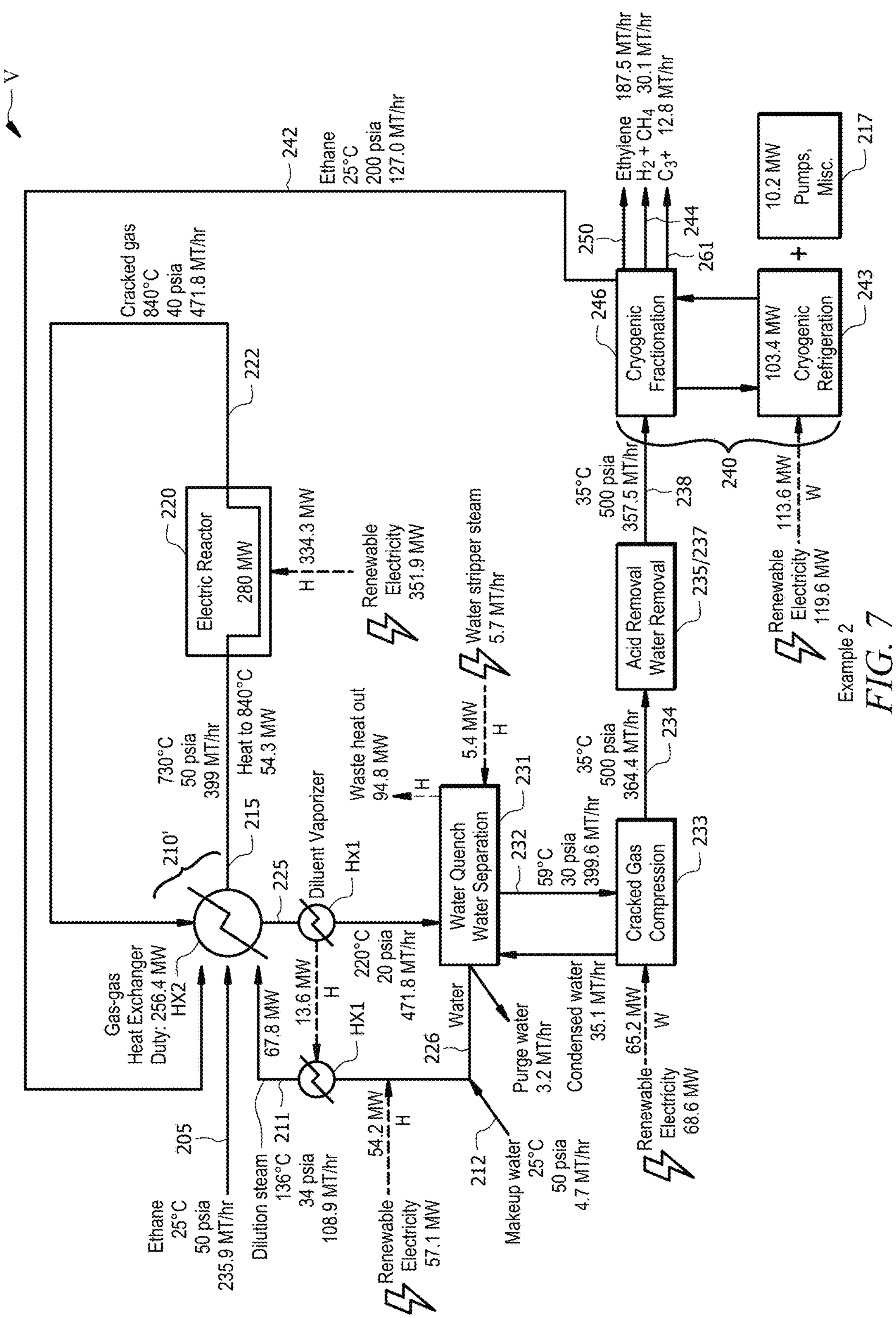
FIG. 7 shows operating parameters for an olefin synthesis plant V electrified as per an embodiment of this disclosure and presented in Example 2.

The key elements of this electrified plant V of Example 2 are shown in FIG. 7. An amount of 236 t/hr of ethane feed 205 are combined with recycle gases in ethane recycle stream 242 and diluent steam in dilution steam 211; the combined feed stream 215 is heated to 730° C. by heat exchange with cooling product gases in a heat exchanger system HX2. This heat exchange can be achieved by a variety of methods, for example one feed/effluent heat exchanger per reactor, a series of feed/effluent heat exchangers, or one or more feed/effluent heat exchangers per reactor together with one or more product heat exchangers using steam to receive the heat coupled with feed heat exchangers in which the energy of the steam is transferred to the feed stream. For the purposes of this example, one feed/effluent heat exchanger per reactor has been employed; however the specific design of the heat exchanger system HX2 can vary, while being configured to extract as much of the heat as possible via cooling the product gases and return it to preheat the feed gases. The feed stream is then cracked at 840° C. in the furnaces of pyrolysis reaction section 220 heated by renewable electricity. The product gases in cracked gas product stream 222 are cooled in a feed/effluent heat exchanger of heat exchanger system HX2 as described above, and further cooled by heat exchange in heat exchanger HX1 of the feed/effluent heat exchanged product in stream 225 with the recycle and makeup water in lines 212 and 226. Diluent water is then recovered by quenching in water quench 231; the recovered water in water line 226 is returned for use as diluent in the pyrolysis reaction section 220. In this embodiment, as indicated in FIG. 7, water quench 231 can involve a water quench tower and a water stripper configured for operation with electricity, rather than steam. The products in quenched cracked gas stream 232 are compressed in cracked gas compression 233, and the compressed cracked gas stream 234 is dried and acid gases are removed in acid gas removal/water removal 235/237 to produce dried cracked gas stream 238. In Example 1, in contrast to the conventional plant described in Comparative Example 1, the heat for the regeneration of the cracked gas drier absorbent material is provided electrically. Dried cracked gas stream 238 is subjected to product fractionation 240 via cryogenic fractionation 246 and associated cryogenic refrigeration 243, which is operated to separate the products and byproducts. Along with the recycle ethane in recycle ethane stream 242, the products and byproducts include 187.5 t/hr of ethylene in ethylene product stream 250, 30 t/hr comprising a mixture of hydrogen and methane in hydrogen- and methane-containing stream 244, and 13 t/hr of $C_{3+}$ products in $C_{3+}$ stream 261 comprising primarily propylene and butadiene.

In addition to a number of smaller users, there are five major energy consumers in the electrified process V of Example 2 (see Table 2): (1) vaporization of the recycle and makeup water (e.g., in heat exchanger HX1) to produce diluent steam, (2) heating of the feed gases to near reaction temperature (e.g., via heat exchanger system HX2), (3) heating of the cracking reactor to supply the final temperature rise to reaction temperature and the heat of reaction (e.g., heating of electric reactor of pyrolysis reaction section 220), (4) energy to drive the cracked gas compressor (e.g., of cracked gas compression 233), and (5) energy to drive the cryogenic fractionation (e.g., cryogenic fractionation 246 of product fractionation section 240). Smaller amounts of energy are used for a variety of other purposes. Some of this energy can be obtained by heat exchange with the product stream as it is cooled, but the rest must be supplied externally. In Example 2, the only external source of energy is renewable electricity. This energy can be allocated to the various consumers of energy in the process with the highest efficiency by careful matching of temperatures, types of energy, and energy content. Some of the energy can be transferred directly via heat exchange. In contrast to Comparative Example 1 and Example 1, in the process of this Example 2 no energy is converted to steam that is used for heat exchange or to do mechanical work, such as drive a compressor. In Example 2 a logical strategy has been adopted for matching heat inputs and outputs, but other arrangements are possible, and intended to be within the scope of this disclosure. In this Example 2, 109 MW of renewable electricity are used to supply energy to the cryogenic fractionation system 240. Because this energy can be applied with high efficiency (assumed here to be 95%), this 109 MW of electrical energy can replace 398 MW of energy supplied as steam in Comparative Example 1. An additional 10 MW of electrical energy is used to supply energy to several water pumps at 217 that were driven by steam in Comparative Example 1, again with much higher efficiency. 57 MW of renewable electricity is also used to supply some of the needed heat for diluent water vaporization. As in Comparative Example 1, some energy is lost in the water quench 231 as well as in other process steps. However, Example 2 according to this disclosure produces no flue gas from combustion, completely eliminating this as a source of energy loss or $CO_2$ emissions.

Table 2 shows an energy balance for the complete electrification process V of Example 2. An amount of 603 MW of renewable electricity are supplied to process; this represents a total net energy input to the process of approximately 53% less than in Comparative Example 1. Additionally, 270 MW are transferred internally during the cooling of the product gases of process V of Example 2, which is electrified according to this disclosure. Unlike in Comparative Example 1, there is no steam system in Example 2 other than the steam used as diluent in the feed. Total losses from the system from inefficiencies in the use of electricity and losses in the quench system and other process steps are 82% less than in Comparative Example 1.

Table 3 provides relevant energy use statistics for Example 2 according to this disclosure. In Example 2, no natural gas is consumed and no $CO_2$ is produced. The 673,000 tons per year of natural gas saved can be used elsewhere, for example as a feed for a methanol or ammonia synthesis process. Specific energy consumption is 11.6 GJ per ton of ethylene produced, which is 53% less than in the process of Comparative Example 1. Only 24% of the net external energy supplied is lost in the water quench 231 and other process steps and the inefficiencies of converting electricity to shaft work (e.g., for cracked gas compression at 233 and cryogenic refrigeration at 243) a significant improvement over Comparative Example 1.

Example 3

Example 3 is a complete electrification as per an embodiment of this disclosure of the steam cracking process described in Comparative Example 1. In this example, in contrast to Example 1, the transfer-line exchanger 223 is retained and the energy captured by it is converted to steam and used for a variety of purposes, while other parts of the process, including feed preheating, the pyrolysis reactor of pyrolysis reaction section 220, and the cracked gas compressor at 233, are electrified.

Figure 8:
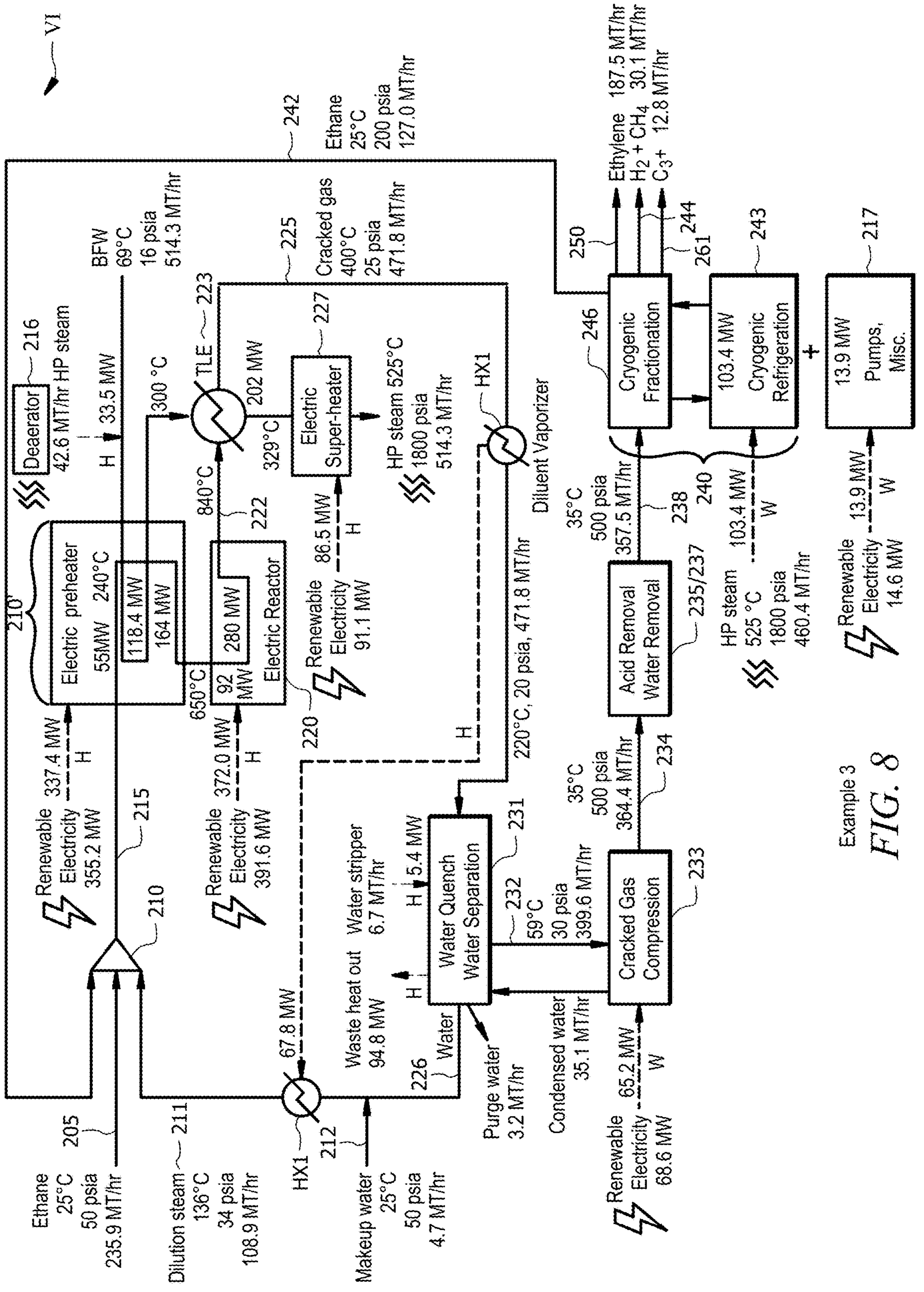
FIG. 8 shows operating parameters for an olefin synthesis plant VI electrified as per an embodiment of this disclosure and presented in Example 3 and FIG. 9 shows operating parameters for an olefin synthesis plant VII electrified as per an embodiment of this disclosure and presented in Examples 4 and 5.

The key elements of this electrified plant VI are shown in FIG. 8. 236 metric tons per hour (t/hr) of ethane feed 205 are fed to the process and combined in a mixer of feed pretreatment section 210 with recycle ethane in ethane recycle stream 242 and diluent steam in dilution steam 211; the combined feed stream 215 is heated to 650° C. in the electric preheater of pre-heating section 210' and then heated to a reaction temperature of 840° C. in the furnaces of pyrolysis reaction section 220 heated by renewable electricity. This reaction section 220 also supplies the heat of reaction for the ethane cracking, which is endothermic. The exiting process gas in cracked gas product stream 222 is cooled to 400° C. in a transfer line exchanger (TLE) 223 and further cooled by exchange of the product in TLE quenched cracked gas stream 225 in heat exchanger HX1 which vaporizes the recycle and makeup water in lines 212 and 226. The diluent water is then recovered by quenching in water quench 231; the recovered water in water line 226 is returned for use as diluent in the pyrolysis reaction section 220. The products in quenched cracked gas stream 232 are compressed in cracked gas compression 233, and the compressed cracked gas stream 234 dried in acid gas removal/water removal 235/237 to produce dried cracked gas stream 238. Dried cracked gas stream 238 is subjected to product fractionation 240 via cryogenic fractionation 246 and associated cryogenic refrigeration 243, which is operated to separate the products and byproducts. Along with the recycle ethane in recycle ethane stream 242, the products and byproducts include 187.5 t/hr of ethylene in ethylene product stream 250, 30 t/hr comprising a mixture of hydrogen and methane in hydrogen- and methane-containing stream 244, and 13 t/hr of $C_{3+}$ products in $C_{3+}$ stream 261 comprising primarily propylene and butadiene In addition to a number of smaller users, there are six major energy consumers in the electrified process VI of Example 3 (see Table 2): (1) vaporization of the recycle and makeup water (e.g., in heat exchanger HX1) to produce steam, (2) heating of the feed gases to near reaction temperature (e.g., via electric pre-heater of pre-heating section 210'), (3) heating of the cracking reactors to supply the final temperature rise to reaction temperature and the heat of reaction (e.g., heating of electric reactor of pyrolysis reaction section 220), (4) power to drive the cracked gas compressor (e.g., of cracked gas compression 233), (5) energy to drive the cryogenic fractionation (e.g., cryogenic fractionation 246 of product fractionation section 240), and (6) superheating of steam in electric superheater 227. Smaller amounts of energy are used for a variety of other purposes. Some of this energy can be obtained by heat exchange with the product stream as it is cooled, but the rest must be supplied externally. In Example 3, the only external source of energy is renewable electricity. This energy can be allocated to the various consumers of energy in the process with the highest efficiency by careful matching of temperatures, types of energy, and energy content. Some of the energy can be transferred directly via heat exchange. In Example 3, a logical strategy has been adopted for matching heat inputs and outputs, but other arrangements are possible, and intended to be within the scope of this disclosure. In this Example 3, 69 MW of renewable electricity are used to supply energy to the cracked gas compression section 233. Because this energy can be applied with high efficiency (assumed here to be 95%), this 69 MW of electrical energy can replace 252 MW of energy supplied as steam in Comparative Example 1. An additional 14 MW of electrical energy is used to supply energy to several water pumps at 217 that were driven by steam in Comparative Example 1, again with much higher efficiency. An amount of 355 MW of renewable electricity is used to supply needed heat for pre-heating the feed as well as the boiler feed water in electric preheating section 210'. An amount of 392 MW of renewable electricity is used to supply needed heat for heating the feed to reaction temperature and for the heat of reaction in electric reactor of pyrolysis reactor section 220. An amount of 91 MW of renewable electricity is used to supply heat for super-heating the high pressure steam in an electric super-heater 227. As in Comparative Example 1, some energy is lost in the water quench 231 as well as in other process steps. However, Example 3 according to this disclosure produces no flue gas from combustion, eliminating this as a source of energy loss or $CO_2$ emissions.

Table 2 shows an energy balance for the complete electrification process VI of Example 3. An amount of 921 MW of renewable electricity is supplied to the process; this represents a total net energy input to the process of 29% less than in Comparative Example 1. Additionally, 310 MW of heat energy are transferred internally according to Example 3 according to this disclosure, primarily from the cooling of the product gases. The total energy supplied to the steam system in Example 3 amounts to 440 MW, which is 42% less than the amount that is required in Comparative Example 1. In Example 3, the majority of this steam energy is used to drive the compressors of cryogenic refrigeration section 243. Total losses from the process described in Example 3, due to inefficiencies in the use of electricity, the inefficiencies in the use of steam to do shaft work, losses in the quench system and other process steps, are 44% less than in Comparative Example 1.

Table 3 provides relevant energy use statistics for Example 3 according to this disclosure. In Example 3, no natural gas is consumed and no $CO_2$ is produced. The 673,000 tons per year of natural gas saved can be used elsewhere, for example as a feed for a methanol synthesis process. Specific energy consumption is 17.7 GJ per ton of ethylene produced, which is 28% less than in the process of Comparative Example 1. In this Example 3, 50% of the net external energy supplied is lost in the water quench 231 and other process steps and the inefficiencies of converting steam or electricity to shaft work (e.g., for cryogenic refrigeration at 243), a significant improvement over Comparative Example 1.

A comparison of Examples 1, 2 and 3 shows some of the trade-offs that arise when considering electrification. Depending on the specific configuration of an existing plant, it may be easier or harder to implement certain modifications, favoring certain types of electrification over others. The best combination of modifications chosen can be determined by one skilled in the art according to the teachings of this disclosure, and such combinations are within the scope of this disclosure.

A comparison of the energy use statistics for Examples 1, 2 and 3 also shows trade-offs when choosing modifications for partial electrification. The energy efficiency of Examples 1 and 2 is higher than that of Example 3, and the total amount of energy used is lower. However, natural gas consumption and $CO_2$ emissions are higher in Example 1 than in Example 3. This is a consequence of how the added renewable energy is used; in Example 1 the electricity is used primarily to do mechanical work, which represents an efficiency gain, while in Example 3 some of the electricity is used to replace fuel supplied to the cracking furnaces, which lowers fuel consumption and $CO_2$ emissions. Which option is preferable will depend on needs and limitations of the plant being modified or designed. In partial electrification, the best combination of modifications can be determined by one skilled in the art according to the teachings of this disclosure, and such combinations are within the scope of this disclosure.

Example 4

Figure 9:
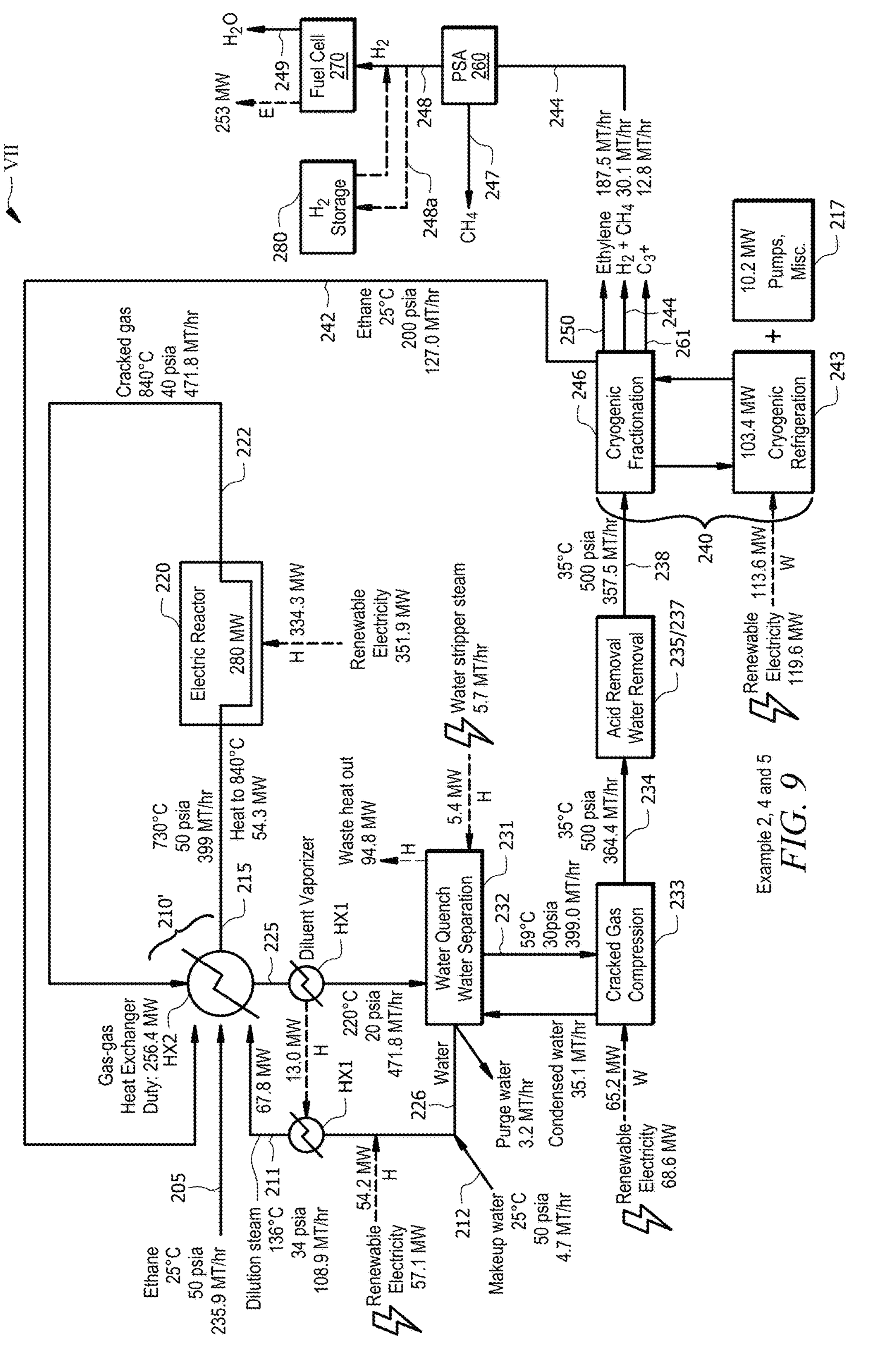

In an embodiment, as depicted in FIG. 9, a process VII comprises a gas separation unit 260 added to the process V described in Example 2. The gas separation unit 260 can comprise a pressure swing adsorption (PSA) unit. The gas separation unit 260 is configured to purify the hydrogen- and methane-containing stream 244. As per Example 2 described hereinabove, stream 244 has a flowrate of 30.1 t/hr and comprises 48 weight % (88 mol %) hydrogen and 52 weight % (12 mol %) methane. The gas separation unit 260 (e.g., PSA gas separation unit 260) consumes 3 MW of electricity, and yields two product streams, a methane stream 247 consisting essentially of pure methane and a hydrogen stream 248 consisting essentially of pure hydrogen. Via this process VII, an amount of 14.3 t/hr of purified hydrogen produced in PSA 260 can be fed to a fuel cell 270, where the hydrogen is converted to water in water stream 249 and electricity E with an electrical efficiency of 45%, giving continuous production of 253 MW of electricity. The net electricity (250 MW) is used to supply 41% of the 603 MW of electricity required for the process (as described hereinabove for process V of Example 2; see Table 2.)

Example 5

In embodiment, a process VII as described in Example 4 further comprises a hydrogen compression and storage apparatus 280 comprising at least one compressor and storage vessel, and configured to compress and store the resulting 14.3 t/hr of purified hydrogen (which can be introduced thereto via line 248A) for use when the availability of renewable electricity is lower, or when it is more expensive. When needed, the compressed and stored hydrogen can be combined (e.g., via line 248B) with the hydrogen being produced at that time (e.g., the hydrogen in line 248) by the process VII, and both can be converted to electricity using the fuel cell 270. When to use the stored hydrogen for electricity production can be determined by one of skill in the art according to a variety of factors. As one possibility, if some renewable electricity is available on a diurnal basis, 172 tons hydrogen could be collected and stored over a twelve hour period. When released over the next twelve hours and combined with the 14.3 t/hr hydrogen still being produced by the process, this would result in approximately 503 MW of electricity being available continuously for the twelve hours. This could supply 80% of the 603 MW of electricity required for the operation of the process.

TABLE 2

Energy Balances for the Processes of Comparative Example 1 and Examples 1-3

| | Comparative Example 1 (all values in MW) | Example 1 (all values in MW) | Example 2 (all values in MW) | Example 3 (all values in MW) |
|---|---|---|---|---|
| Energy inputs: | | | | |
| Cracking Furnaces of Pyrolysis Reaction Section 220 | 920 | 737 | 0 | 0 |

TABLE 2-continued

Energy Balances for the Processes of Comparative Example 1 and Examples 1-3

| | Comparative Example 1 (all values in MW) | Example 1 (all values in MW) | Example 2 (all values in MW) | Example 3 (all values in MW) |
|---|---|---|---|---|
| Auxiliary Boiler 221 | 369 | 0 | 0 | 0 |
| External Electricity | 0 | 135 | 603 | 921 |
| Subtotal: Net External Energy | 1289 | 872 | 603 | 921 |
| Deaerator 216 | 33.5 | 20 | 0 | 33.5 |
| TLE 223 or Feed/effluent heat exchanger of HX2 | 202 | 256 | 256 | 202 |
| Vaporizer HX1 | 68 | 14 | 14 | 68 |
| Water stripper of water quench 231 | 5.4 | 5.4 | 0 | 5.4 |
| Demethanizer generator | 1.6 | 1.6 | 1.6 | 1.6 |
| Total | 1599 | 1169 | 875 | 1231 |
| Heat usage: | | | | |
| Feed Preheat | 219 | 256 | 256 | 0 |
| Diluent Vaporization HX1 | 68 | 14 | 14 | 68 |
| Cracking Reactor of Pyrolysis Reaction Section 220 | 372 | 335 | 0 | 0 |
| Steam generation | 759 | 323 | 0 | 202 |
| Total | 1418 | 927 | 270 | 270 |
| Steam Usage: | | | | |
| Deaerator 216 | 33.5 | 20 | 0 | 33.5 |
| Diluent vaporization HX1 | 0 | 43 | 0 | 0 |
| Water quench 231 | 5.4 | 5.4 | 0 | 5.4 |
| Cracked Gas Compressor at 233 | 65 | 65 | 0 | 0 |
| Cryogenic Refrigeration at 243 | 103 | 0 | 0 | 103 |
| Other pumps, misc. at 217 | 19 | 0 | 0 | 0 |
| Total | 226 | 134 | 0 | 142 |
| Electric usage: | | | | |
| Steam preheat and superheat | 0 | 0 | 0 | 205 |
| Diluent Vaporization at HX1 | 0 | 11.5 | 54 | 0 |
| Feed preheat | 0 | 0 | 0 | 219 |
| Cracking Reactor of Pyrolysis Reaction Section 220 | 0 | 0 | 334 | 372 |
| Water quench 231 | 0 | 0 | 5.4 | 0 |
| Cracked Gas Compressor at 233 | 0 | 0 | 65 | 65 |
| Cryogenic Refrigeration at 243 | 0 | 103 | 103 | 0 |
| Other pumps, misc. at 217 | 1.5 | 15 | 11 | 15 |
| Total | 1.5 | 130 | 573 | 877 |
| Energy Losses: | | | | |
| Stack Losses | 174 | 99 | 0 | 0 |
| Process Losses | 113 | 113 | 113 | 113 |
| Losses due to inefficiency in steam usage | 533 | 189 | 0 | 298 |
| Losses due to inefficiency in electrical usage | 0.1 | 6.8 | 31 | 46 |
| Total | 820 | 408 | 144 | 457 |

TABLE 3

Energy Use Statistics for the Processes of Comparative Example 1 and Example 1-3

| | Comparative Example 1 | Example 1 | Example 2 | Example 3 |
|---|---|---|---|---|
| Natural Gas Consumption | 673,000 t/yr | 385,000 t/yr | 0 t/yr | 0 t/yr |
| Specific Energy Consumption | 24.7 GJ/t | 16.7 GJ/t | 11.6 GJ/t | 17.7 GJ/t |
| $CO_2$ Emissions | 1,850,000 t/yr | 1,058,000 t/yr | 0 t/yr | 0 t/yr |
| Energy Losses | 64% | 47% | 24% | 50% |

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k^*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Disclosure Part I

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising." "containing." or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: An olefin synthesis plant for the production of light olefins, the olefin synthesis plant comprising: a feed pretreatment section configured to pretreat a feed stream; a pyrolysis section comprising one or more pyrolysis reactors configured to crack hydrocarbons in the feed stream in the presence of a diluent to produce a cracked gas stream; a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that, relative to a conventional olefin synthesis plant, more of the energy and/or the net energy required by the olefin synthesis plant, the feed pretreatment section, the pyrolysis section, the primary fractionation and compression section, the product separation section, or a combination thereof, is provided by a non-carbon based energy source, a renewable energy source and/or electricity.

B: An olefin synthesis plant for the production of light olefins, the olefin synthesis plant comprising: a feed pretreatment section configured to pretreat a feed stream; a pyrolysis section comprising one or more pyrolysis reactors configured to crack hydrocarbons in the feed stream in the presence of a diluent to produce a cracked gas stream; a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that a majority of the process energy and/or the net process energy required by the olefin synthesis plant, the feed pretreatment section, the pyrolysis section, the primary fractionation section, the product separation section, or a combination thereof, is provided by electricity.

C: Apparatus described herein for carrying out the method as in any of the embodiments described in this disclosure.

Each of embodiments A, B, and C may have one or more of the following additional elements: Element 1: wherein the non-carbon based energy source comprises electricity. Element 2: wherein the electricity is produced from a renewable energy source, and/or wherein the renewable energy source comprises wind, solar, geothermal, hydroelectric, nuclear, tidal, wave, or a combination thereof. Element 3: wherein a predetermined cracking temperature within the one or more pyrolysis reactors is attained without combusting a fuel, a carbon-based fuel, and/or a fossil fuel. Element 4: wherein no fuel, carbon-based fuel, or fossil fuel is combusted within the olefin synthesis plant. Element 5: wherein the amount of $CO_2$ produced per ton of ethylene produced is reduced to less than 1.2 tons $CO_2$ per ton of ethylene. Element 6: wherein the specific energy consumption calculated from the net energy inputs is less than 17 GJ/ton. Element 7: wherein the amount of electricity consumed is greater than or equal to 50 MW. Element 8: wherein the one or more pyrolysis reactors are heated to the predetermined cracking temperature via resistive and/or inductive heating. Element 9: wherein the one or more pyrolysis reactors are heated to the predetermined cracking temperature via a radiant section in which heat generated electrically is used to heat radiative panels which transfer heat to the one or more pyrolysis reactors by radiation. Element 10: wherein the diluent comprises steam. Element 11: wherein: other than the production of steam for use as the diluent in the one or more pyrolysis reactors and/or to facilitate heat transfer with the cracked gas stream, steam is not produced for use as a primary energy transfer medium. Element 12: wherein: a majority, some, or all of the steam utilized as the diluent in the one or more pyrolysis reactors, one or more, a majority, or all steam turbines of the plant, or a combination thereof is produced electrically. Element 13: wherein the primary fractionation and compression section, the product separation section, or both comprise one or more compressors, and wherein at least half or a majority of the one or more compressors are configured for non-gas-driven or non-steam driven operation. Element 14: wherein the primary fractionation and compression section, the product separation section, or both comprise one or more compressors, and wherein at least one of the one or more compressors are configured for bifunctional operation via both electric motor-driven and gas-driven or electric motor-driven and steam driven operation. Element 15: wherein the primary fractionation and compression section, the product separation section, or both comprise one or more compressors, and further comprising dual drive compressors for one or more compression step of the primary fractionation and compression section, the product separation section, or both, such that the compression step can be effected via a first of the dual drives that is online when a second of the dual drives is offline, and vice versa, wherein the first of the dual drives is electric motor-driven, and the second of the dual drives is steam-driven or combustion-driven. Element 16: wherein configuration of the plant enables operation of one or more compressors via renewable electricity, when available, and operation via combustion-produced steam or gas combustion, when renewable electricity is not available. Element 17: wherein the renewable electricity is provided by wind, solar, geothermal, hydroelectric, nuclear, tide, wave, or a combination thereof. Element 18: wherein the primary fractionation and compression section, the product separation section, or both comprise one or more distillation columns and associated reboilers, and wherein at least a part of the energy for one or more distillation columns is supplied and/or removed electrically. Element 19: further comprising stored energy in the form of compressed hydrogen, compressed hydrocarbon(s) of the feed, compressed hydrocarbon(s) of the products, cryogenic liquids, thermal batteries, electric batteries, or a combination thereof, such that the stored energy from the compressed hydrogen, the compressed hydrocarbon(s) from the feed, compressed hydrocarbon(s) of the products, the cryogenic liquids, the thermal batteries, the electric batteries, or the combination thereof can be utilized when renewable electricity is not available. Element 20: comprising: (a) storage for a compressed ethane or LPG feed at high pressure, wherein the stored, compressed ethane or LPG feed can later be expanded to generate electricity and subsequently used as a feed; (b) storage for compressed ethane or propane feed at low temperature, wherein the stored, compressed ethane or LPG feed can later be used as a refrigerant and, subsequently utilized as a feed; or (c) a combination thereof. Element 21: further comprising electricity production apparatus configured to produce electricity from pressure or heat within the olefin synthesis plant. Element 22: wherein the electricity production apparatus comprises an expander, a thermoelectric device, or a combination thereof. Element 23: wherein the one or more pyrolysis reactors are configured for cracking a gaseous or liquid hydrocarbon feed comprising naphtha, ethane, propane, butane, LPG, condensate, gas oil, unconverted hydrowax (hydrocracker bottoms), Fischer-Tropsch wax, hydrotreated crude oil and crude oil derivatives, pyrolysis oil from recycled plastics, bio-oils, biodiesel, bionaphtha, or a combination thereof. Element 24: configured such that no steam is used to do mechanical work within the olefin synthesis plant. Element 25: configured for the production of no combustion flue gas. Element 26: further comprising one or more fuel cells operable to generate electricity from hydrogen produced within the olefin synthesis plant. Element 27: configured to export hydrogen produced within the olefin synthesis plant to an ammonia synthesis plant and/or to convert the hydrogen produced within the olefin synthesis plant to ammonia via reaction with nitrogen. Element 28: configured to export methane produced within the olefin synthesis plant to a methanol synthesis plant and/or to convert the methane produced within the olefin synthesis plant to methanol.

Additional Disclosure Part II

The following are non-limiting, specific embodiments in accordance with the present disclosure:

A first embodiment, which is an olefin synthesis plant for the production of light olefins, the olefin synthesis plant comprising a feed pretreatment section configured to pre-treat a feed stream, a pyrolysis section comprising one or more pyrolysis reactors configured to crack hydrocarbons in the feed stream in the presence of a diluent to produce a cracked gas stream, a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that, relative to a conventional olefin synthesis plant, more of the energy and/or the net energy required by the olefin synthesis plant, the feed pretreatment section, the pyrolysis section, the primary fractionation and compression section, the product separation section, or a combination thereof, is provided by a non-carbon based energy source, a renewable energy source and/or electricity.

A second embodiment, which is the olefin synthesis plant of the first embodiment, wherein the non-carbon based energy source comprises electricity.

A third embodiment, which is an olefin synthesis plant for the production of light olefins, the olefin synthesis plant comprising a feed pretreatment section configured to pre-treat a feed stream, a pyrolysis section comprising one or more pyrolysis reactors configured to crack hydrocarbons in the feed stream in the presence of a diluent to produce a cracked gas stream, a primary fractionation and compression section configured to provide heat recovery from and quenching of the cracked gas stream; remove fuel oil, hydrogen sulfide, carbon dioxide, water, pyrolysis gasoline, or a combination thereof from the cracked gas stream; and compress the cracked gas stream, thus providing a compressed cracked gas stream; and/or a product separation section configured to separate a product olefin stream from the compressed cracked gas stream, wherein the olefin synthesis plant is configured such that a majority of the process energy and/or the net process energy required by the olefin synthesis plant, the feed pretreatment section, the pyrolysis section, the primary fractionation section, the product separation section, or a combination thereof, is provided by electricity.

A fourth embodiment, which is the olefin synthesis plant of the second, or the third embodiment, wherein the electricity is produced from a renewable energy source, and/or wherein the renewable energy source comprises wind, solar, geothermal, hydroelectric, nuclear, tidal, wave, or a combination thereof.

A fifth embodiment, which is the olefin synthesis plant of the first, the second, or the third embodiment, wherein a predetermined cracking temperature within the one or more pyrolysis reactors is attained without combusting a fuel, a carbon-based fuel, and/or a fossil fuel.

A sixth embodiment, which is the olefin synthesis plant of the first, the second, or the third embodiment, wherein no fuel, carbon-based fuel, or fossil fuel is combusted within the olefin synthesis plant.

A seventh embodiment, which is the olefin synthesis plant of the first, the second, or the third embodiment, wherein the amount of $CO_2$ produced per ton of ethylene produced is reduced to less than 1.2 tons $CO_2$ per ton of ethylene.

An eighth embodiment, which is the olefin synthesis plant of the first, the second, or the third embodiment, wherein the specific energy consumption calculated from the net energy inputs is less than 17 GJ/ton.

A ninth embodiment, which is the olefin synthesis plant of the first, the second, or the third embodiment, wherein the amount of electricity consumed is greater than or equal to 50 MW.

A tenth embodiment, which is the olefin synthesis plant of the first, the second, or the third embodiment, wherein the one or more pyrolysis reactors are heated to the predetermined cracking temperature via resistive and/or inductive heating.

An eleventh embodiment, which is the olefin synthesis plant of the first, the second, or the third embodiment, wherein the one or more pyrolysis reactors are heated to the predetermined cracking temperature via a radiant section in which heat generated electrically is used to heat radiative panels which transfer heat to the one or more pyrolysis reactors by radiation.

A twelfth embodiment, which is the olefin synthesis plant of the first, the second, or the third embodiment, wherein the diluent comprises steam.

A thirteenth embodiment, which is the olefin synthesis plant of the twelfth embodiment, wherein other than the production of steam for use as the diluent in the one or more pyrolysis reactors and/or to facilitate heat transfer with the cracked gas stream, steam is not produced for use as a primary energy transfer medium.

A fourteenth embodiment, which is the olefin synthesis plant of the twelfth embodiment, wherein a majority, some, or all of the steam utilized as the diluent in the one or more pyrolysis reactors, one or more, a majority, or all steam turbines of the plant, or a combination thereof is produced electrically.

A fifteenth embodiment, which is the olefin synthesis plant of the first, the second, or the third embodiment, wherein the primary fractionation and compression section, the product separation section, or both comprise one or more compressors, and wherein at least half or a majority of the one or more compressors are configured for non-gas-driven or non-steam driven operation.

A sixteenth embodiment, which is the olefin synthesis plant of the first, the second, or the third embodiment, wherein the primary fractionation and compression section, the product separation section, or both comprise one or more compressors, and wherein at least one of the one or more compressors are configured for bifunctional operation via both electric motor-driven and gas-driven or electric motor-driven and steam driven operation.

A seventeenth embodiment, which is the olefin synthesis plant of the first, the second, or the third embodiment, wherein the primary fractionation and compression section, the product separation section, or both comprise one or more compressors, and further comprising dual drive compressors for one or more compression step of the primary fractionation and compression section, the product separation section, or both, such that the compression step can be effected via a first of the dual drives that is online when a second of the dual drives is offline, and vice versa, wherein the first of the dual drives is electric motor-driven, and the second of the dual drives is steam-driven or combustion-driven.

An eighteenth embodiment, which is the olefin synthesis plant of the fifteenth, the sixteenth, or the seventeenth embodiment, wherein configuration of the plant enables operation of one or more compressors via renewable electricity, when available, and operation via combustion-produced steam or gas combustion, when renewable electricity is not available.

A nineteenth embodiment, which is the olefin synthesis plant of any of the fifteenth through the eighteenth embodiments, wherein the renewable electricity is provided by wind, solar, geothermal, hydroelectric, nuclear, tide, wave, or a combination thereof.

A twentieth embodiment, which is the olefin synthesis plant of the first, the second, or the third embodiment, wherein the primary fractionation and compression section, the product separation section, or both comprise one or more distillation columns and associated reboilers, and wherein at least a part of the energy for one or more distillation columns is supplied and/or removed electrically.

A twenty-first embodiment, which is the olefin synthesis plant of the first, the second, or the third embodiment further comprising stored energy in the form of compressed hydrogen, compressed hydrocarbon(s) of the feed, compressed hydrocarbon(s) of the products, cryogenic liquids, thermal batteries, electric batteries, or a combination thereof, such that the stored energy from the compressed hydrogen, the compressed hydrocarbon(s) from the feed, compressed hydrocarbon(s) of the products, the cryogenic liquids, the thermal batteries, the electric batteries, or the combination thereof can be utilized when renewable electricity is not available.

A twenty-second embodiment, which is the olefin synthesis plant of the twenty-first embodiment, comprising: (a) storage for a compressed ethane or LPG feed at high pressure, wherein the stored, compressed ethane or LPG feed can later be expanded to generate electricity and subsequently used as a feed; (b) storage for compressed ethane or propane feed at low temperature, wherein the stored, compressed ethane or LPG feed can later be used as a refrigerant and, subsequently utilized as a feed; or (c) a combination thereof.

A twenty-third embodiment, which is the olefin synthesis plant of the first, the second, or the third embodiment, further comprising electricity production apparatus configured to produce electricity from pressure or heat within the olefin synthesis plant.

A twenty-fourth embodiment, which is the olefin synthesis plant of the twenty-third embodiment, wherein the electricity production apparatus comprises an expander, a thermoelectric device, or a combination thereof.

A twenty-fifth embodiment, which is the olefin synthesis plant of the first, the second, or the third embodiment, wherein the one or more pyrolysis reactors are configured for cracking a gaseous or liquid hydrocarbon feed comprising naphtha, ethane, propane, butane, LPG, condensate, gas oil, unconverted hydrowax (hydrocracker bottoms), Fischer-Tropsch wax, hydrotreated crude oil and crude oil derivatives, pyrolysis oil from recycled plastics, bio-oils, biodiesel, bionaphtha, or a combination thereof.

A twenty-sixth embodiment, which is the olefin synthesis plant of the first, the second, or the third embodiment, configured such that no steam is used to do mechanical work within the olefin synthesis plant.

A twenty-seventh embodiment, which is the olefin synthesis plant of the first, the second, or the third embodiment, configured for the production of no combustion flue gas.

A twenty-eighth embodiment, which is the olefin synthesis plant of the first, the second, or the third embodiment further comprising one or more fuel cells operable to generate electricity from hydrogen produced within the olefin synthesis plant.

A twenty-ninth embodiment, which is the olefin synthesis plant of the first, the second, or the third embodiment, configured to export hydrogen produced within the olefin synthesis plant to an ammonia synthesis plant and/or to convert the hydrogen produced within the olefin synthesis plant to ammonia via reaction with nitrogen.

A thirtieth embodiment, which is the olefin synthesis plant of the first, the second, or the third embodiment, configured to export methane produced within the olefin synthesis plant to a methanol synthesis plant and/or to convert the methane produced within the olefin synthesis plant to methanol.

A thirty-first embodiment, which is apparatus described herein for carrying out the method as in any of the embodiments described in this disclosure.

Additional Disclosure Part III

The following are non-limiting, specific embodiments in accordance with the present disclosure:

Embodiments disclosed herein include:

A: A method of producing olefins, the method comprising: (a) cracking a feed stream comprising hydrocarbons to produce a cracked gas comprising olefins, wherein cracking the feed stream comprises increasing the temperature of the feed stream to a cracking temperature; (b) recovering heat from the cracked gas comprising olefins; (c) compressing the cracked gas to provide a compressed, cracked gas; (d) removing acid gas from the compressed, cracked gas; (e) drying the acid gas-reduced cracked gas to produce a dried, cracked gas; (f) cooling the dried, cracked gas to provide a cooled, cracked gas; (g) separating one or more olefins from the cooled, cracked gas; or (h) a combination thereof, wherein, relative to a conventional method of producing olefins via steam cracking, more of the energy and/or the net energy required (a), (b), (c), (d), (e), (f), (g) or (h) is provided by a non-carbon based energy source, a renewable energy source, and/or electricity.

B: A method of producing olefins, the method comprising: (a) cracking a feed stream comprising hydrocarbons to produce a cracked gas comprising olefins, wherein cracking the feed stream comprises increasing the temperature of the feed stream to a cracking temperature; (b) recovering heat from the cracked gas; (c) compressing the cracked gas to provide a compressed, cracked gas; (d) removing acid gas from the compressed, cracked gas; (e) drying the acid gas-reduced cracked gas to produce a dried, cracked gas; (f) cooling the cracked gas to provide a cooled, cracked gas; (g) separating one or more olefins from the cooled, cracked gas; or (h) a combination thereof, wherein a majority of the energy and/or the net energy needed in (a), (b), (c), (d), (e), (f), (g), or (h) is provided by electricity.

Each of embodiments A and B may have one or more of the following additional elements: Element 1: wherein the non-carbon based energy source comprises electricity. Element 2: wherein the electricity is produced from a renewable energy source, and/or wherein the renewable energy source comprises wind, solar, geothermal, hydroelectric, nuclear, tidal, wave, or a combination thereof. Element 3: wherein increasing the temperature of the feed stream to the cracking temperature is effected without combusting a fuel, a carbon-based fuel, and/or a fossil fuel. Element 4: wherein no combusting of fuel, carbon-based fuel, and/or fossil fuel is utilized for heating. Element 5: wherein the non-carbon based energy source comprises or the electricity is produced via an intermittent energy source (IES), and wherein any of steps (a) through (h) or a combination thereof is effected without combusting a fuel, a carbon-based fuel, and/or a fossil fuel when the IES is available, and is effected via a stored supply of energy from the IES and/or by combusting a fuel, a carbon-based fuel, and/or a fossil fuel when the IES is not available. Element 6: wherein (a) is carried out in one or more pyrolysis reactors that are heated to the desired cracking temperature via electric heating. Element 7: wherein the electric heating comprises resistive and/or inductive heating. Element 8: wherein, (b) recovering heat from the cracked gas comprises producing steam, and wherein, other than the production of steam in (b), steam is not utilized as a primary energy transfer medium. Element 9: wherein: (i) steam is not produced; (ii) steam is not produced and utilized other than as a diluent in (a); or (iii) (b) recovering heat from the cracked gas comprises producing steam, which is utilized solely to preheat the feed stream. Element 10: wherein (a) comprises increasing the temperature of the feed stream to the cracking temperature by electrically heating the feed stream in a radiant section; injecting steam or superheated steam into a cracking reactor, wherein the steam or the superheated steam is produced electrically; heating the feed stream by impedance; heating by induction; heating via a heat pump; heating the feed stream by passing over a resistively heated element; heating by passing a hot, inert gas or other hot medium over tubes of a cracking reactor, wherein the hot gas or heated medium is heated electrically; heating the feed stream with a heat exchanger comprising electrical heating elements; heating the feed stream via resistive heating; heating the feed stream directly by ohmic heating, plasma, electric arc, RF, IR, UV, microwaves or a combination thereof; heating the feed stream by a thermoelectric device; heating the feed stream via an electrically-driven mechanical means; or a combination thereof. Element 11: wherein (b) recovering heat from the cracked gas does not comprise the production of steam. Element 12: wherein (b) recovering heat from the cracked gas comprises: direct heat exchange between the cracked gas and the feed stream; indirect heat exchange between the cracked gas and the feed stream via one or more heat exchanges at one or more temperatures wherein a heat-transfer fluid is used only to move the heat from the cracked gas to the feed stream; extracting heat via a cracked gas cooler coupled with a thermoelectric device for generating electricity; or a combination thereof. Element 13: wherein (b) comprises utilization of a cold fluid, and: wherein heat introduced into the cold fluid during a water quench is utilized to heat the feed stream to the cracking temperature; wherein the cold fluid is coupled with a thermoelectric device to generate electricity; wherein an absorption chiller is utilized to cool the cold fluid such that the cracked gas is electrically cooled to a lower than conventional temperature; wherein the cold fluid is coupled to a heat pump; wherein a thermoelectric device is utilized to modify a temperature of the cold fluid; wherein an electric heater is utilized to modify a temperature of the cold fluid; or a combination thereof. Element 14: wherein an electric heater is utilized to heat a process water stripper reboiler; wherein an electrode boiler is utilized to vaporize recycled process water to produce steam utilized as a diluent in (a); wherein an electric heater is utilized to produce steam or superheated steam; or a combination thereof. Element 15: wherein (c) compressing the cracked gas to provide a compressed, cracked gas comprises a compressor driven with an electric motor rather than a steam turbine in at least one compression stage of a multiple stage primary cracked gas compression; compressing with an electric-drive compressor; increasing or decreasing the pressure of the compressed, cracked gas relative to a conventional method; utilizing a thermoelectric device integrated into one or more vapor/liquid separators upstream of at least one compression stage; or a combination thereof. Element 16: wherein (d) removing acid gas from the compressed, cracked gas comprises an amine system, wherein a stripper is heated with an electric heater. Element 17: wherein (e) drying the acid gas-reduced cracked gas to produce a dried, cracked gas comprises contacting the acid gas-reduced cracked gas with a solid moisture adsorbent, and periodically regenerating the solid moisture adsorbent with: a drying gas that is heated with electricity; electrically heating a dryer vessel utilized for the drying; utilizing a closed-loop system for the drying and condensing water from a regeneration gas; or a combination thereof. Element 18: wherein (f) comprises cryogenically cooling the dried, cracked gas to provide a cooled, cracked gas by: cooling via one or more refrigeration compressors, wherein a majority or all of the refrigeration compressors are electrified; utilizing a greater number of refrigeration compressors and/or compression stages than conventional, and tailoring each of the one or more refrigeration compressors and/or compression stages; utilizing an unconventional working fluid (e.g., nitrogen or carbon dioxide); recovering energy conventionally lost at one or more pressure let down steps as electricity; utilizing direct electric cooling (e.g., thermoelectric device(s)) rather than conventional refrigeration; or a combination thereof. Element 19: wherein the method produces a stream comprising primarily methane and hydrogen, and wherein the method further comprises: introducing at least a portion of the stream comprising primarily methane and hydrogen to a process for the production of methanol or ammonia; or (i) separating hydrogen from the stream comprising primarily methane and hydrogen, wherein (i) separating hydrogen from the stream comprising primarily methane and hydrogen comprises: optionally compressing the stream comprising primarily methane and hydrogen via an electrified compressor to provide a compressed stream comprising methane and hydrogen, and separating the compressed stream comprising methane and hydrogen into a stream comprising methane and a stream comprising hydrogen; and storing the stream comprising hydrogen when an IES source is available (e.g., during the day), and utilizing a fuel cell to make electricity from the stored stream comprising hydrogen when an IES source is not available (e.g., during the night); and/or exporting the stream comprising hydrogen (e.g., to an ammonia plant or a methanol plant). Element 20: wherein the energy required for (a) is obtained solely from heat exchange with the cracked gas and electricity. Element 21: wherein a diluent steam utilized in (a) is generated and heated electrically. Element 22: wherein some of the energy required for (a) is obtained by superheating a diluent stream to above the temperature of (a) to provide a superheated diluent stream, and combining the superheated diluent stream with the feed stream. Element 23: wherein electric heating is used to impose a temperature profile on one or more cracking reactors utilized in (a).

Additional Disclosure Part IV

The following are non-limiting, specific embodiments in accordance with the present disclosure:

A first embodiment, which is a method of producing olefins, the method comprising (a) cracking a feed stream comprising hydrocarbons to produce a cracked gas comprising olefins, wherein cracking the feed stream comprises increasing the temperature of the feed stream to a cracking temperature, (b) recovering heat from the cracked gas comprising olefins, (c) compressing the cracked gas to provide a compressed, cracked gas, (d) removing acid gas from the compressed, cracked gas, (e) drying the acid gas-reduced cracked gas to produce a dried, cracked gas, (f) cooling the dried, cracked gas to provide a cooled, cracked gas, (g) separating one or more olefins from the cooled, cracked gas, or (h) a combination thereof, wherein, relative to a conventional method of producing olefins via steam cracking, more of the energy and/or the net energy required (a), (b), (c), (d), (e), (f), (g) or (h) is provided by a non-carbon based energy source, a renewable energy source, and/or electricity.

A second embodiment, which is the method of the first embodiment, wherein the non-carbon based energy source comprises electricity.

A third embodiment, which is a method of producing olefins, the method comprising (a) cracking a feed stream comprising hydrocarbons to produce a cracked gas comprising olefins, wherein cracking the feed stream comprises increasing the temperature of the feed stream to a cracking temperature, (b) recovering heat from the cracked gas, (c) compressing the cracked gas to provide a compressed, cracked gas, (d) removing acid gas from the compressed, cracked gas, (e) drying the acid gas-reduced cracked gas to produce a dried, cracked gas, (f) cooling the cracked gas to provide a cooled, cracked gas, (g) separating one or more olefins from the cooled, cracked gas, or (h) a combination thereof, wherein a majority of the energy and/or the net energy needed in (a), (b), (c), (d), (e), (f), (g), or (h) is provided by electricity.

A fourth embodiment, which is the method of the second or the third embodiment, wherein the electricity is produced from a renewable energy source, and/or wherein the renewable energy source comprises wind, solar, geothermal, hydroelectric, nuclear, tidal, wave, or a combination thereof.

A fifth embodiment, which is the method of the second or the third embodiment, wherein increasing the temperature of the feed stream to the cracking temperature is effected without combusting a fuel, a carbon-based fuel, and/or a fossil fuel.

A sixth embodiment, which is the method of the second or the third embodiment, wherein no combusting of fuel, carbon-based fuel, and/or fossil fuel is utilized for heating.

A seventh embodiment, which is the method of the second or the third embodiment, wherein the non-carbon based energy source comprises or the electricity is produced via an intermittent energy source (IES), and wherein any of steps (a) through (h) or a combination thereof is effected without combusting a fuel, a carbon-based fuel, and/or a fossil fuel when the IES is available, and is effected via a stored supply of energy from the IES and/or by combusting a fuel, a carbon-based fuel, and/or a fossil fuel when the IES is not available.

An eighth embodiment, which is the method of the second or the third embodiment, wherein (a) is carried out in one or more pyrolysis reactors that are heated to the desired cracking temperature via electric heating.

A ninth embodiment, which is the method of the eighth embodiment, wherein the electric heating comprises resistive and/or inductive heating.

A tenth embodiment, which is the method of the first, the second, or the third embodiment, wherein, (b) recovering heat from the cracked gas comprises producing steam, and wherein, other than the production of steam in (b), steam is not utilized as a primary energy transfer medium.

An eleventh embodiment, which is the method of the first, the second, or the third embodiment, wherein (i) steam is not produced, (ii) steam is not produced and utilized other than as a diluent in (a), or (iii) (b) recovering heat from the cracked gas comprises producing steam, which is utilized solely to preheat the feed stream.

A twelfth embodiment, which is the method of the second or the third embodiment, wherein (a) comprises increasing the temperature of the feed stream to the cracking temperature by electrically heating the feed stream in a radiant section; injecting steam or superheated steam into a cracking reactor, wherein the steam or the superheated steam is produced electrically; heating the feed stream by impedance; heating by induction; heating via a heat pump; heating the feed stream by passing over a resistively heated element; heating by passing a hot, inert gas or other hot medium over tubes of a cracking reactor, wherein the hot gas or heated medium is heated electrically; heating the feed stream with a heat exchanger comprising electrical heating elements; heating the feed stream via resistive heating; heating the feed stream directly by ohmic heating, plasma, electric arc, RF, IR, UV, microwaves or a combination thereof; heating the feed stream by a thermoelectric device; heating the feed stream via an electrically-driven mechanical means; or a combination thereof.

A thirteenth embodiment, which is the method of the first, the second, or the third embodiment, wherein (b) recovering heat from the cracked gas does not comprise the production of steam.

A fourteenth embodiment, which is the method of the first, the second, or the third embodiment, wherein (b) recovering heat from the cracked gas comprises: direct heat exchange between the cracked gas and the feed stream; indirect heat exchange between the cracked gas and the feed stream via one or more heat exchanges at one or more temperatures wherein a heat-transfer fluid is used only to move the heat from the cracked gas to the feed stream; extracting heat via a cracked gas cooler coupled with a thermoelectric device for generating electricity; or a combination thereof.

A fifteenth embodiment, which is the method of the second or the third embodiment, wherein (b) comprises utilization of a cold fluid, and wherein heat introduced into the cold fluid during a water quench is utilized to heat the feed stream to the cracking temperature, wherein the cold fluid is coupled with a thermoelectric device to generate electricity, wherein an absorption chiller is utilized to cool the cold fluid such that the cracked gas is electrically cooled to a lower than conventional temperature, wherein the cold fluid is coupled to a heat pump, wherein a thermoelectric device is utilized to modify a temperature of the cold fluid, wherein an electric heater is utilized to modify a temperature of the cold fluid, or a combination thereof.

A sixteenth embodiment, which is the method of the second or the third embodiment wherein an electric heater is utilized to heat a process water stripper reboiler, wherein an electrode boiler is utilized to vaporize recycled process water to produce steam utilized as a diluent in (a), wherein an electric heater is utilized to produce steam or superheated steam, or a combination thereof.

A seventeenth embodiment, which is the method of the second or the third embodiment, wherein (c) compressing the cracked gas to provide a compressed, cracked gas comprises a compressor driven with an electric motor rather than a steam turbine in at least one compression stage of a multiple stage primary cracked gas compression; compressing with an electric-drive compressor; increasing or decreasing the pressure of the compressed, cracked gas relative to a conventional method; utilizing a thermoelectric device integrated into one or more vapor/liquid separators upstream of at least one compression stage; or a combination thereof.

An eighteenth embodiment, which is the method of the second or the third embodiment, wherein (d) removing acid gas from the compressed, cracked gas comprises an amine system, wherein a stripper is heated with an electric heater.

A nineteenth embodiment, which is the method of the second or the third embodiment, wherein (e) drying the acid gas-reduced cracked gas to produce a dried, cracked gas comprises contacting the acid gas-reduced cracked gas with a solid moisture adsorbent, and periodically regenerating the solid moisture adsorbent with: a drying gas that is heated with electricity; electrically heating a dryer vessel utilized for the drying; utilizing a closed-loop system for the drying and condensing water from a regeneration gas; or a combination thereof.

A twentieth embodiment, which is the method of the second or the third embodiment, wherein (f) comprises cryogenically cooling the dried, cracked gas to provide a cooled, cracked gas by: cooling via one or more refrigeration compressors, wherein a majority or all of the refrigeration compressors are electrified; utilizing a greater number of refrigeration compressors and/or compression stages than conventional, and tailoring each of the one or more refrigeration compressors and/or compression stages; utilizing an unconventional working fluid (e.g., nitrogen or carbon dioxide); recovering energy conventionally lost at one or more pressure let down steps as electricity; utilizing direct electric cooling (e.g., thermoelectric device(s)) rather than conventional refrigeration; or a combination thereof.

A twenty-first embodiment, which is the method of the second or the third embodiment, wherein the method produces a stream comprising primarily methane and hydrogen, and wherein the method further comprises introducing at least a portion of the stream comprising primarily methane and hydrogen to a process for the production of methanol or ammonia, or (i) separating hydrogen from the stream comprising primarily methane and hydrogen, wherein (i) separating hydrogen from the stream comprising primarily methane and hydrogen comprises optionally compressing the stream comprising primarily methane and hydrogen via an electrified compressor to provide a compressed stream comprising methane and hydrogen, and separating the compressed stream comprising methane and hydrogen into a stream comprising methane and a stream comprising hydrogen, and storing the stream comprising hydrogen when an IES source is available (e.g., during the day), and utilizing a fuel cell to make electricity from the stored stream comprising hydrogen when an IES source is not available (e.g., during the night), and/or exporting the stream comprising hydrogen (e.g., to an ammonia plant or a methanol plant).

A twenty-second embodiment, which is the method of the second or the third embodiment, wherein the energy required for (a) is obtained solely from heat exchange with the cracked gas and electricity.

A twenty-third embodiment, which is the method of the second or the third embodiment, wherein a diluent steam utilized in (a) is generated and heated electrically.

A twenty-fourth embodiment, which is the method of the second or the third embodiment, wherein some of the energy required for (a) is obtained by superheating a diluent stream to above the temperature of (a) to provide a superheated diluent stream, and combining the superheated diluent stream with the feed stream.

A twenty-fifth embodiment, which is the method of the second or the third embodiment, wherein electric heating is used to impose a temperature profile on one or more cracking reactors utilized in (a).

Additional Disclosure Part V

The following are non-limiting, specific embodiments in accordance with the present disclosure:

A first embodiment, which is an olefin synthesis plant for the production of light olefins, the olefin synthesis plant comprising a feed pretreatment section configured to pretreat a feed stream, one or more furnaces, wherein at least one of the one or more furnaces is configured to be an electrified furnace, and wherein each electrified furnace further comprises a pyrolysis section comprising one or more pyrolysis reactors configured to crack hydrocarbons in the feed stream in the presence of a diluent to produce a cracked gas stream, a primary fractionation and compression section configured to (a) provide heat recovery from and quenching of the cracked gas stream; (b) remove fuel oil, hydrogen sulfide, carbon dioxide, water, pyrolysis gasoline, or a combination thereof from the cracked gas stream; and (c) compress the cracked gas stream, thus providing a compressed cracked gas stream, and a product separation section configured to separate a product olefin stream comprising at least ethylene from the compressed cracked gas stream, wherein each electrified furnace is configured such that at least 90% of heating throughout each electrified furnace is produced without combusting a fuel, a carbon-based fuel, a fossil fuel, or combinations thereof, and wherein olefin synthesis plant is configured to consume greater than or equal to 10, 20, 30, 40, 50, 60, 70, 80, 90, or 100 MW of electrical power. In an aspect, one, a plurality, or all of the one or more furnaces of the first embodiment may be electrified furnaces. In another aspect, the one or more furnaces of the first embodiment that are electrified furnaces are configured to (i) consume greater than or equal to 10, 20, 30, 40, 50, 60, 70, 80, 90, or 100 MW of electrical power per furnace, (ii) consume greater than or equal to 10, 20, 30, 40, 50, 60, 70, 80, 90, or 100 MW of electrical power in total (e.g., all electrified furnaces in combination), or (iii) both (i) and (ii).

A second embodiment, which is the olefin synthesis plant according to the first embodiment, where each electrified furnace has no flue gas heat recovery section.

A third embodiment, which is the olefin synthesis plant according to the first or the second embodiment, wherein at least 10, 20, 30, 40, 50, 60, 70, 80, 90, 95, 99, or 100% of the mechanical work in the olefin synthesis plant is generated without use of steam.

A fourth embodiment, which is the olefin synthesis plant according to any of the first through the third embodiments, wherein the amount of $CO_2$ produced per ton of ethylene produced is reduced to less than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 tons CO2 per ton of ethylene generated in the olefin synthesis plant.

A fifth embodiment, which is the olefin synthesis plant according to any of the first through the fourth embodiments, wherein the specific energy consumption calculated from the net energy inputs in each electrified furnace is less than 17 GJ/ton.

A sixth embodiment, which is the olefin synthesis plant according to any of the first through the fifth embodiments, wherein the one or more pyrolysis reactors are heated to the predetermined cracking temperature via resistive heating.

A seventh embodiment, which is the olefin synthesis plant according to any of the first through the sixth embodiments, wherein the one or more pyrolysis reactors are heated to the predetermined cracking temperature via inductive heating.

An eighth embodiment, which is the olefin synthesis plant according to any of the first through the seventh embodiments, wherein the one or more pyrolysis reactors are heated to the predetermined cracking temperature via a radiant section in which heat generated electrically is used to directly transfer heat to one or more pyrolysis reactors by radiation or to heat radiative panels which transfer heat to the one or more pyrolysis reactors by radiation or by a combination of these methods A ninth embodiment, which is the olefin synthesis plant according to any of the first through the eighth embodiments, wherein other than the production of steam for use as the diluent in the one or more pyrolysis reactors or to facilitate heat transfer with the cracked gas stream, steam is not produced for use as a primary energy transfer medium.

A tenth embodiment, which is the olefin synthesis plant according to any of the first through the ninth embodiments, further comprising storing energy in the form of compressed hydrogen, compressed hydrocarbon(s) of the feed, compressed hydrocarbon(s) of the products, cryogenic liquids, thermal batteries, electric batteries, or a combination thereof, such that the stored energy can be utilized when renewable electricity is not available.

An eleventh embodiment, which is the olefin synthesis plant according to the ninth embodiment, comprising: (a) storage for a compressed ethane or LPG feed at high pressure, wherein the stored, compressed ethane or LPG feed can later be expanded to generate electricity and subsequently used as a feed; (b) storage for compressed ethane or propane feed at low temperature, wherein the stored, compressed ethane or LPG feed can later be used as a refrigerant and, subsequently utilized as a feed; or (c) a combination thereof.

A twelfth embodiment, which is the olefin synthesis plant according to the ninth embodiment, comprising: (a) storage for a compressed ethene and/or propene or a combination thereof interim product at high pressure, wherein the stored, compressed ethene and/or propene interim product can later be expanded to generate electricity and subsequently used as final product; (b) storage for compressed ethene or propene interim product at low temperature, wherein the stored, compressed ethene and/or propene interim product can later be used as a refrigerant and, subsequently utilized as a final product; or (c) a combination thereof.

A thirteen embodiment, which is a method of producing olefins, the method comprising (a) cracking a feed stream comprising hydrocarbons to produce a cracked gas comprising olefins, wherein cracking the feed stream comprises increasing the temperature of the feed stream to a cracking temperature, (b) recovering heat from the cracked gas comprising olefins, (c) compressing the cracked gas to provide a compressed, cracked gas, (d) removing acid gas from the compressed, cracked gas, (e) drying the acid gas-reduced cracked gas to produce a dried, cracked gas, (f) cooling the dried, cracked gas to provide a cooled, cracked gas, and (g) separating one or more olefins comprising at least ethylene from the cooled, cracked gas, wherein the amount of $CO_2$ produced per ton of ethylene produced is reduced to less than 0.5 tons $CO_2$ per ton of ethylene, wherein at least 50% of heating during the method is produced without combusting a fuel, a carbon-based fuel, a fossil fuel, or combinations thereof, and wherein the method consumes greater than or equal to 10, 20, 30, 40, 50, 60, 70, 80, 90, or 100 MW of electrical power.

A fourteenth embodiment, which is the method according to the thirteenth embodiment, wherein at least 90% of heat requirements for increasing the temperature of the feed stream to the cracking temperature is effected without combusting a fuel, a carbon-based fuel, a fossil fuel, or combinations thereof.

A fifteenth embodiment, which is the method according to the thirteen or the fourteenth embodiment, wherein at least 90% of heating during the method is accomplished with no combusting of a fuel, a carbon-based fuel, a fossil fuel, or combinations thereof.

A sixteenth embodiment, which is the method according to any of the thirteenth through the fifteenth embodiments, wherein (b) recovering heat from the cracked gas comprises producing steam, and wherein other than the production of steam in (b), steam is not utilized as a primary energy transfer medium.

A seventeenth embodiment, which is the method according to any of the thirteenth through the sixteenth embodiments, wherein (i) steam is not produced. (ii) steam is not produced and utilized other than as a diluent in (a), or (iii) (b) recovering heat from the cracked gas comprises producing steam, which is utilized solely to preheat the feed stream, but no other steam is produced and utilized other than as a diluent in (a).

An eighteenth embodiment, which is the method according to any of the thirteenth through the seventeenth embodiments, wherein (b) recovering heat from the cracked gas comprises: direct heat exchange between the cracked gas and the feed stream; indirect heat exchange between the cracked gas and the feed stream via one or more heat exchanges at one or more temperatures wherein a heat-transfer fluid is used only to move the heat from the cracked gas to the feed stream; extracting heat via a cracked gas cooler coupled with a thermoelectric device for generating electricity; or a combination thereof.

A nineteenth embodiment, which is the method according to any of the thirteenth through the eighteenth embodiments wherein an electric heater is utilized to heat a process water stripper reboiler, wherein an electric boiler is utilized to vaporize recycled process water to produce steam utilized as a diluent in (a), wherein an electric heater is utilized to produce steam or superheated steam, or a combination thereof.

A twentieth embodiment, which is the method according to any of the thirteenth through the nineteenth embodiments, wherein a diluent steam utilized in (a) is generated and heated electrically.

A twenty-first embodiment, which is the method according to any of the thirteenth through the twentieth embodiments, wherein some of the energy required for (a) is obtained by superheating a diluent stream to above the temperature of (a) to provide a superheated diluent stream, and combining the superheated diluent stream with the feed stream.

A twenty-second embodiment, which is the method according to any of the thirteenth through the twenty-first embodiments, wherein electric heating is used to impose a temperature profile on one or more cracking reactors utilized in (a).

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. An olefin synthesis plant for the production of light olefins, the olefin synthesis plant comprising:
- a feed pretreatment section configured to pretreat a feed stream;
- a diluent heater configured to heat a diluent;
- one or more furnaces, wherein at least one of the one or more furnaces is configured to supply heat without combusting a fuel, and wherein each furnace further comprises a pyrolysis section comprising one or more pyrolysis reactors configured to crack hydrocarbons in the pretreated feed stream to produce a cracked gas stream;
- a primary fractionation and compression section configured to (a) provide heat recovery from and quenching of the cracked gas stream; (b) remove fuel oil, hydrogen sulfide, carbon dioxide, water, pyrolysis gasoline, or a combination thereof from the cracked gas stream; and (c) compress the cracked gas stream, thus providing a compressed cracked gas stream;
- a product separation section configured to separate a product olefin stream comprising at least ethylene and a hydrogen-containing stream from the compressed cracked gas stream; and
- a fuel cell configured to produce electricity from hydrogen recovered from the hydrogen-containing stream,
- wherein the olefin synthesis plant is configured such that at least 90% of the net energy used for heating the feed stream, the furnace, and the diluent is provided by electricity.

2. The olefin synthesis plant of claim 1, wherein the olefin synthesis plant is configured to produce greater than or equal to 10,000 tons of ethylene per year.

3. The olefin synthesis plant of claim 1, wherein the olefin synthesis plant is configured to consume greater than or equal to 50 MW of electricity.

4. The olefin synthesis plant of claim 1, wherein the feed pretreatment section comprises an electric feed preheater configured to heat the feed stream.

5. The olefin synthesis plant of claim 1, wherein the feed pretreatment section comprises a mixer configured to mix the feed stream and the diluent heated by the diluent heater.

6. The olefin synthesis plant of claim 1, wherein the feed stream comprises recycled plastic.

7. The olefin synthesis plant of claim 1, wherein the product separation section is further configured to separate an ethane recycle stream from the compressed cracked gas stream.

8. The olefin synthesis plant of claim 7, further comprising a recycle line configured to recycle the ethane recycle stream to the feed pretreatment section or the one or more furnaces.

9. The olefin synthesis plant of claim 7, further comprising a hydrogen purification apparatus configured to recover hydrogen from the hydrogen-containing stream.

10. A method of producing light olefins in the olefin synthesis plant according to claim 1, the method comprising:
- providing a feed stream to the feed pretreatment section to form a pretreated feed stream;
- providing a diluent to the diluent heater to form a heated diluent;
- providing the pretreated feed stream and the heated diluent to the one or more furnaces to crack hydrocarbons in the pretreated feed stream to produce a cracked gas stream;
- providing the cracked gas stream to the primary fractionation and compression section to compress the cracked gas stream to form a compressed cracked gas stream; and
- providing the compressed cracked gas stream to the product separation section to separate a product olefin stream comprising at least ethylene and a hydrogen stream from the compressed cracked gas stream.

11. An olefin synthesis plant for the production of light olefins, the olefin synthesis plant comprising:
- a feed pretreatment section configured to pretreat a feed stream;
- one or more furnaces, wherein at least one of the one or more furnaces is configured to be an electrified furnace, and wherein each electrified furnace further comprises a pyrolysis section comprising one or more pyrolysis reactors configured to crack hydrocarbons in the pretreated feed stream in the presence of a diluent to produce a cracked gas stream;
- a primary fractionation and compression section configured to (a) provide heat recovery from and quenching of the cracked gas stream; (b) remove fuel oil, hydrogen sulfide, carbon dioxide, water, pyrolysis gasoline, or a combination thereof from the cracked gas stream; and (c) compress the cracked gas stream, thus providing a compressed cracked gas stream;
- a heat exchanger positioned between an inlet to the primary fractionation and compression section and an outlet from the furnace and configured to transfer heat from the cracked gas stream to the feed stream; and
- a product separation section configured to separate a product olefin stream comprising at least ethylene from the compressed cracked gas stream;
- wherein the olefin synthesis plant is configured such that at least 90% of electricity used for heating in each electrified furnace is provided to the electrified furnace without combusting a fuel, a carbon-based fuel, a fossil fuel, or combinations thereof.

12. The olefin synthesis plant of claim 11, wherein the feed stream comprises recycled plastic.

13. The olefin synthesis plant of claim 11, wherein the product separation section is further configured to separate a hydrogen-containing stream from the compressed cracked gas stream.

14. The olefin synthesis plant of claim 13, further configured to export hydrogen in the hydrogen-containing stream to an ammonia synthesis plant and/or convert the hydrogen to ammonia via a reaction with nitrogen in the olefin synthesis plant.

15. The olefin synthesis plant of claim 11, wherein the diluent comprises steam.

16. The olefin synthesis plant of claim 15, wherein the steam is produced electrically.

17. The olefin synthesis plant of claim 11, further comprising one or more fuel cells operable to generate electricity from hydrogen produced within the olefin synthesis plant.

18. The olefin synthesis plant of claim 17, wherein the olefin synthesis plant is configured to produce greater than or equal to 10,000 tons of ethylene per year.

19. A method for producing light olefins in the olefin synthesis plant according to claim 11, the method comprising:

providing a feed stream to the feed pretreatment section to form a pretreated feed stream;

providing the pretreated feed stream to the one or more furnaces to crack hydrocarbons in the pretreated feed stream in the presence of a diluent to produce a cracked gas stream;

providing the cracked gas stream to the feed pretreatment section to transfer heat from the cracked gas stream to the feed stream and form a cooled cracked gas stream;

providing the cooled cracked gas stream to the primary fractionation and compression section to form a compressed cracked gas stream; and providing the compressed cracked gas stream to the product separation section to separate a product olefin stream comprising at least ethylene from the compressed cracked gas stream.

* * * * *